(12) United States Patent
Shi

(10) Patent No.: US 11,696,729 B2
(45) Date of Patent: Jul. 11, 2023

(54) SYSTEMS AND METHODS FOR IMAGE DATA ACQUISITION

(71) Applicant: SHANGHAI UNITED IMAGING HEALTHCARE CO., LTD., Shanghai (CN)

(72) Inventor: Yuhang Shi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 503 days.

(21) Appl. No.: 16/870,924

(22) Filed: May 9, 2020

(65) Prior Publication Data
US 2021/0128076 A1 May 6, 2021

(30) Foreign Application Priority Data
Nov. 1, 2019 (CN) .......................... 201911059466.8

(51) Int. Cl.
| | | |
|---|---|---|
| *G06K 9/00* | (2022.01) | |
| *A61B 5/00* | (2006.01) | |
| *G16H 40/67* | (2018.01) | |
| *G16H 10/60* | (2018.01) | |
| *G16H 50/20* | (2018.01) | |
| *A61B 5/0245* | (2006.01) | |
| *A61B 5/055* | (2006.01) | |
| *A61B 6/03* | (2006.01) | |
| *G01R 33/567* | (2006.01) | |
| *G06N 3/04* | (2023.01) | |
| *G06N 5/04* | (2023.01) | |
| *G06T 7/00* | (2017.01) | |
| *A61B 6/00* | (2006.01) | |
| *G01R 33/56* | (2006.01) | |

(52) U.S. Cl.
CPC .......... *A61B 5/7285* (2013.01); *A61B 5/0245* (2013.01); *A61B 5/055* (2013.01); *A61B 5/7264* (2013.01); *A61B 6/037* (2013.01); *G01R 33/5673* (2013.01); *G06N 3/04* (2013.01); *G06N 5/04* (2013.01); *G06T 7/0016* (2013.01); *G16H 10/60* (2018.01); *G16H 40/67* (2018.01); *G16H 50/20* (2018.01); *A61B 5/0035* (2013.01); *A61B 6/5247* (2013.01); *G01R 33/56* (2013.01); *G06T 2207/10104* (2013.01); *G06T 2207/20081* (2013.01)

(58) Field of Classification Search
None
See application file for complete search history.

(56) References Cited

U.S. PATENT DOCUMENTS

| | | | |
|---|---|---|---|
| 2018/0144465 A1* | 5/2018 | Hsieh | ........................ G06N 3/08 |
| 2018/0144466 A1* | 5/2018 | Hsieh | .................... G06T 7/0012 |
| 2019/0133480 A1* | 5/2019 | Rahman | ................. G16H 50/20 |

* cited by examiner

*Primary Examiner* — Wei Wen Yang
(74) *Attorney, Agent, or Firm* — Metis IP LLC

(57) ABSTRACT

The present disclosure provides a system and method for image data acquisition. The method may include acquiring physiological data of a subject. The physiological data may correspond to a motion of the subject over time. The method may include obtaining a trained machine learning model configured to detect feature data represented in the physiological data. The method may include determining, based on the physiological data, an output result of the trained machine learning model that is generated based on the feature data. The method may include acquiring, based on the output result, image data of the subject using an imaging device.

20 Claims, 13 Drawing Sheets

SYSTEMS AND METHODS FOR IMAGE DATA ACQUISITION

CROSS-REFERENCE TO RELATED APPLICATIONS

This application claims priority to Chinese Patent Application No. 201911059466.8, filed on Nov. 1, 2019, the contents of which are hereby incorporated by reference.

TECHNICAL FIELD

The disclosure generally relates to medical system and method, and more particularly relates to model based controlling of medical systems and methods.

BACKGROUND

A medical procedure directed to a subject may be adversely affected by a physiological motion of the subject. For instance, chest and/or abdomen scanning of magnetic resonance imaging (MRI) and/or positron emission tomography (PET) may be often affected by respiratory movement and heartbeat. For example, the cardiac and/or respiratory movement may lead to loss of MR signals, thereby affecting the quality of the image. In order to reduce the effects of the cardiac and/or respiratory movement on the quality of the image, a gating acquisition technique may be widely used for image data acquisition, such as an electrocardiogram gating technique, a pulse gating technique, a respiratory gating technique, etc. Using a gating acquisition technique for image data acquisition, one or more R waves may be detected from physiological data (e.g., ECG data). However, in an imaging scan, various factors, such as a patient with heart disease, a magnetic field of an MR scanner, etc., may cause poor accuracy of R wave detection. Thus, it is desired to provide systems and methods for controlling the execution of a medical procedure to improve its accuracy and/or efficiency by reducing the impact of a physiological motion.

SUMMARY

According to a first aspect of the present disclosure, a system is provided. The system may include at least one storage device storing executable instructions, and at least one processor in communication with the at least one storage device. When executing the executable instructions, the at least one processor may cause the system to perform one or more of the following operations. The system may acquire physiological data of a subject. The physiological data may correspond to a motion of the subject over time. The system may obtain a trained machine learning model. The system may determine, based on the physiological data, an output result of the trained machine learning model. The system may acquire, based on the output result, image data of the subject using an imaging device.

In some embodiments, the physiological data may include at least one of electrocardiogram (ECG) data or respiration data.

In some embodiments, the output result may include at least one of: the feature data represented in the physiological data; a determination as to whether a trigger condition for triggering the imaging device to acquire the image data is satisfied; or a gating weighting function defined by a plurality of weighting values corresponding to the physiological data.

In some embodiments, the feature data may include position information associated with at least one of a peak of an R wave, a rising edge of the R wave, a falling edge of the R wave in the physiological data, a peak of a P wave, a rising edge of the P wave, or a falling edge of the P wave in the physiological data.

In some embodiments, to acquire, based on the output result, image data of the subject using an imaging device, the at least one processor may be configured to cause the system to perform the following operations. In response to determining that the trigger condition is satisfied, the system may generate a trigger pulse signal based on the output result. The system may also cause the imaging device to scan the subject based at least in part on the trigger pulse signal.

In some embodiments, the trigger pulse signal may include a trigger delay for acquiring the image data from a reference time point.

In some embodiments, to acquire, based on the output result, image data of the subject using an imaging device, the at least one processor may be configured to cause the system to perform the following operations. The system may acquire original image data of the subject by the imaging device synchronously with the acquisition of the physiological data by the monitoring device. The system may also determine the image data from the original image data based on the feature data or the gating weighting function.

In some embodiments, the physiological data may be acquired by a monitoring device based on at least one of: an echo signal generated by emitting, by the monitoring device, an electromagnetic wave to the subject, an ECG signal, a photoelectric signal generated by emitting, by the monitoring device, light beams to the subject, an oscillation signal generated when the monitoring device detects an oscillation caused by a motion of the subject, or a pressure signal generated when the monitoring device detects a pressure change caused by the motion of the subject.

In some embodiments, the trained machine learning model may be provided by a process. The process may include obtaining a plurality of training samples. The process may also include initializing parameter values of a machine learning model. The process may further include generating the trained machine learning model by iteratively updating, based on the plurality of training samples, the parameter values of the machine learning model.

In some embodiments, the iteratively updating, based on the plurality of training samples, the parameter values of the machine learning model may include performing an iterative process. Each iteration of the iterative process may include inputting at least one training sample of the plurality of training samples into the machine learning model. Each iteration of the iterative process may include generating, based on the at least one training sample, an estimated output using the machine learning model. Each iteration of the iterative process may include obtaining an assessment result by assessing a difference between the estimated output and a reference output corresponding to the at least one training sample. Each iteration of the iterative process may include determining whether a termination condition is satisfied. Based on a determination whether the termination condition is satisfied, each iteration of the iterative process may include updating, based on the assessment result, at least some of the parameter values of the machine learning model in response to the determination that the termination condition is not satisfied; or designating the machine learning model with the parameter values updated in a last iteration as the deep machine learning model in response to the determination that the termination condition is satisfied.

In some embodiments, the obtaining an assessment result by assessing a difference between the estimated output and a reference output may include determining a value of a cost function relating to the difference between the estimated output and the reference output.

In some embodiments, the cost function may include a Softmax cross entropy loss function or a square error loss function.

In some embodiments, the plurality of training samples may include a plurality of positive samples and a plurality of negative samples. In some embodiments, each of the plurality of positive samples may include first physiological data that includes feature data located within a specific section of a time period of the first physiological data, and each of the plurality of negative samples may include second physiological data that lacks the feature data located within the specific section of a time period of the second physiological data.

In some embodiments, a length of the specific section of the time period may be less than a length of an acquisition window of the imaging device for acquiring the image data.

In some embodiments, to determine, based on the physiological data, an output result of a trained machine learning model, the at least one processor may be configured to cause the system to perform the following operations. The system may perform a pretreatment operation on the physiological data to obtain preprocessed physiological data. The system may also generate the output result by inputting the preprocessed physiological data into the trained machine learning model.

In some embodiments, the pretreatment operation may include at least one of a normalization operation, a denoising operation, a smoothing operation, or a downsampling operation.

According to a second aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain a plurality of training samples. Each of the plurality of training samples including physiological data of a subject. The system may generate a trained machine learning model by training, based on the plurality of training samples, a machine learning model. In some embodiments, the trained machine learning model may be configured to perform at least one of: determining feature data represented in specific physiological data of a specific subject; determining whether a trigger condition for triggering an imaging device to acquire image data of the specific subject is satisfied based on the specific physiological data; or determining a gating weighting function defined by a plurality of weighting values corresponding to the specific physiological data based on the specific physiological data.

In some embodiments, to generate a trained machine learning model by training, based on the plurality of training samples, a machine learning model, the at least one processor may be configured to cause the system to perform the following operations. The system may obtain a plurality of training samples. The system may also initialize parameter values of a machine learning model. The system may further generate the trained machine learning model by iteratively updating, based on the plurality of training samples, the parameter values of the machine learning model.

In some embodiments, the iteratively updating, based on the plurality of training samples, the parameter values of the machine learning model may include performing an iterative process. Each iteration of the iterative process may include inputting at least one training sample of the plurality of training samples into the machine learning model. Each iteration of the iterative process may include generating, based on the at least one training sample, an estimated output using the machine learning model. Each iteration of the iterative process may include obtaining an assessment result by assessing a difference between the estimated output and a reference output corresponding to the at least one training sample. Each iteration of the iterative process may include determining whether a termination condition is satisfied. Based on a determination whether the termination condition is satisfied, each iteration of the iterative process may include updating, based on the assessment result, at least some of the parameter values of the machine learning model in response to the determination that the termination condition is not satisfied; or designating the machine learning model with the parameter values updated in a last iteration as the deep machine learning model in response to the determination that the termination condition is satisfied.

According to a second aspect of the present disclosure, a method is provided. The method may acquire physiological data of a subject, the physiological data corresponding to a motion of the subject over time. The method may also obtain a trained machine learning model configured to detect feature data represented in the physiological data. The method may further determine, based on the physiological data, an output result of the trained machine learning model that is generated based on the feature data. The method may further acquire, based on the output result, image data of the subject using an imaging device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not scaled. These embodiments are non-limiting exemplary embodiments, in which like reference numerals represent similar structures throughout the several views of the drawings, and wherein.

DETAILED DESCRIPTION

Figure 1:
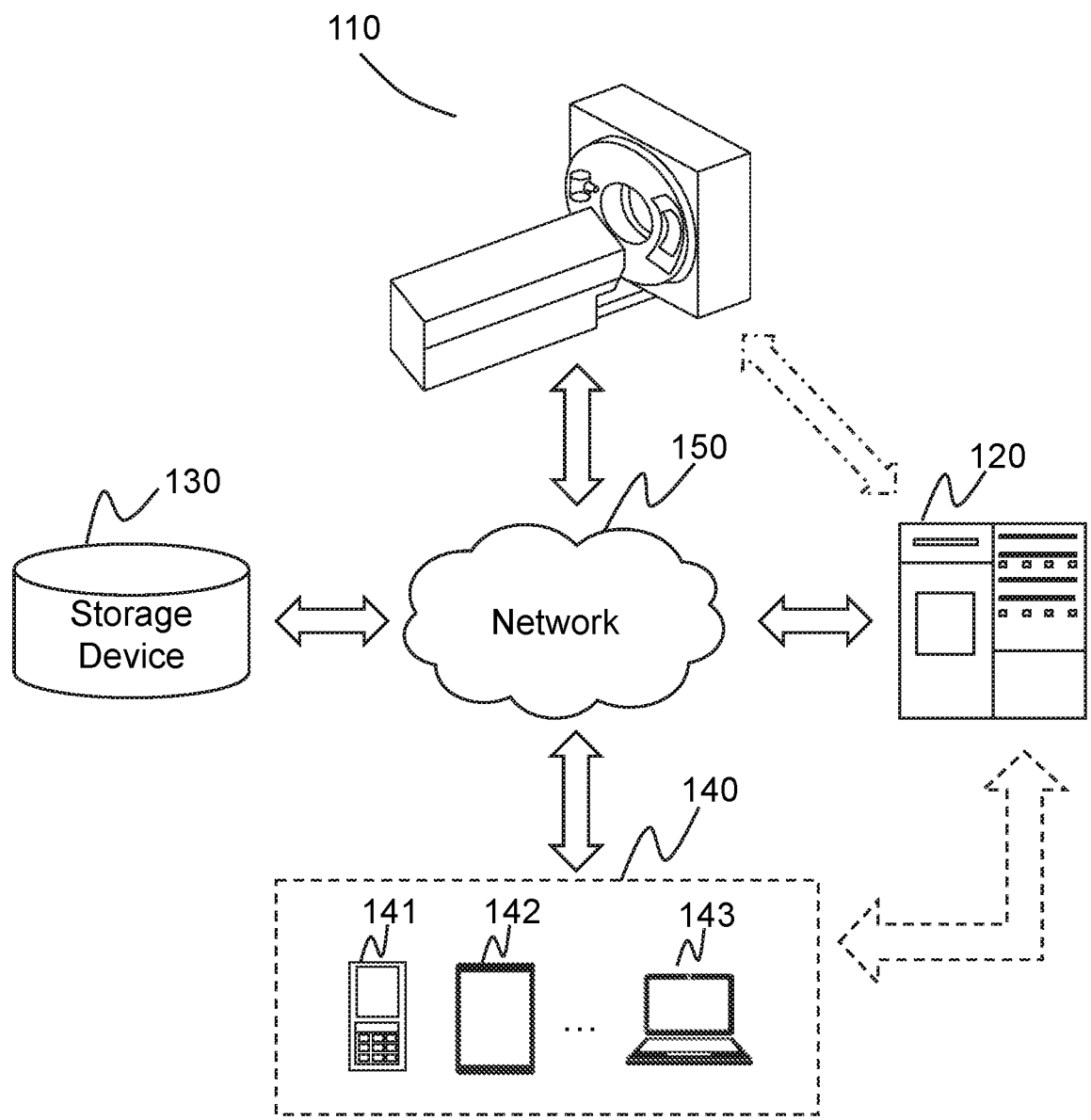
FIG. 1 is a schematic diagram illustrating an exemplary medical system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/ block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/ units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Provided herein are systems and methods for controlling the execution of a medical procedure to improve its accuracy and/or efficiency by reducing the impact of a physiological motion. The medical procedure may be an imaging procedure (e.g., including scanning and/or image reconstruction) or a treatment procedure. The medical procedure may be performed according to a model based control mechanism. For instance, the model may include a trained machine learning model. A system may include at least one storage device storing executable instructions, and at least one processor in communication with the at least one storage device. When executing the executable instructions, the at least one processor may cause the system to obtain physiological data of a subject acquired by a monitoring device. The physiological data may correspond to a motion of the subject over time. The at least one processor may also cause the system to determine an output result, e.g., feature data represented in the physiological data, based on a trained machine learning model. The at least one processor may further cause the medical device to perform the medical procedure including, e.g., obtaining image data of the subject acquired by an imaging device. In some embodiments, the at least one processor may trigger the imaging device to acquire the image data according to the identified feature data (e.g., R waves in the physiological data which include an ECG signal or a respiratory signal, P waves, T waves, Q waves, S waves in the ECG signal).

In some embodiments, the trained machine learning model may be provided by training a machine learning model using a plurality of training samples. For instance, the training samples may include physiological data of R waves of ECG signals. In a training process, the trained machine learning model may not only learn characteristics (e.g., shapes, peak values, locations, change rates, etc.) of R waves from the plurality of training samples, but also identify the characteristics of R waves based on other waves (e.g., a T wave, a P wave, etc.) associated with the R waves. Accordingly, systems and methods as described in the present disclosure may analyze the physiological data including motion information based on the trained machine learning model, and control the execution of the medical procedure accordingly, thereby decreasing a probability of incorrect trigger of the execution of the medical procedure, e.g., image data acquisition, using a gating acquisition technique, and improving the quality of the medical procedure. The output result of the trained machine learning model may also be used in a subsequent analysis of data, e.g., image data, acquired during the medical procedure so that the motion information embedded in the data are accounted for in the subsequent analysis (e.g., image reconstruction), thereby improving the quality of the image(s) so obtained.

FIG. 1 is a schematic diagram illustrating an exemplary medical system according to some embodiments of the present disclosure. In some embodiments, the medical system 100 may be a single-modality system or a multi-modality system. Exemplary single-modality systems may include a magnetic resonance (MR) system, a positron emission tomography (PET) system, a single-photon emission computed tomography (SPECT) system, etc. Exemplary multi-modality systems may include a magnetic resonance-positron emission tomography (MR-PET) system, a PET-CT system, etc. In some embodiments, the medical system 100 may include modules and/or components for performing imaging and/or related analysis.

Merely by way of example, as illustrated in FIG. 1, the medical system 100 may include a medical device 110, a processing device 120, a storage device 130, one or more terminals 140, and a network 150. The components in the medical system 100 may be connected in one or more of various ways. Merely by way of example, the medical device 110 may be connected to the processing device 120 through the network 150. As another example, the medical device 110 may be connected to the processing device 120 directly as illustrated in FIG. 1. As a further example, the terminal(s) 140 may be connected to another component of the medical system 100 (e.g., the processing device 120) via the network 150. As still a further example, the terminal(s) 140 may be connected to the processing device 120 directly as illustrated by the dotted arrow in FIG. 1. As still a further example, the storage device 130 may be connected to another component of the medical system 100 (e.g., the processing device 120) directly as illustrated in FIG. 1, or through the network 150.

The medical device 110 may be configured to acquire image data relating to at least one part of a subject and/or perform a treatment (e.g., radiotherapy) on the at least one part of the subject. The image data relating to at least one part of a subject may include an image (e.g., an image slice), projection data, or a combination thereof. In some embodiments, the image data may be a two-dimensional (2D) image data, a three-dimensional (3D) image data, a four-dimensional (4D) image data, or the like, or any combination thereof. The subject may be biological or non-biological. For example, the subject may include a patient, a man-made object, etc. As another example, the subject may include a specific portion, organ, and/or tissue of the patient. For example, the subject may include the head, the neck, the thorax, the heart, the stomach, a blood vessel, soft tissue, a tumor, nodules, or the like, or any combination thereof. In some embodiments, the medical device 110 may include a single modality imaging device. For example, the medical device 110 may include a positron emission tomography (PET) device, a single-photon emission computed tomography (SPECT) device, a magnetic resonance imaging (MRI) device (also referred to as an MR device, an MR scanner), a computed tomography (CT) device, or the like, or any combination thereof. In some embodiments, the medical device 110 may include a multi-modality imaging device. Exemplary multi-modality imaging devices may include a PET-CT device, a PET-MRI device, or the like, or a combination thereof. For example, the medical device 110 may include a PET device and an MRI device. The PET device may scan a subject or a portion thereof that is located within its detection region and generate projection data relating to the subject or the portion thereof. The following descriptions are provided with reference to an imaging device as the medical device 110, unless otherwise stated. It is understood that this is for illustration purposes and not intended to be limiting.

The processing device 120 may process data and/or information obtained from the medical device 110, the terminal(s) 140, and/or the storage device 130. For example, the processing device 120 may acquire physiological data of a subject using a monitoring device. The physiological data may correspond to a motion of the subject over time. The processing device 120 may determine feature data represented in the physiological data based on a trained machine learning model. The processing device 120 may further cause, based on the feature data, the medical device 110 to execute a medical procedure, e.g., acquiring image data of the subject using an imaging device or performing a treatment procedure by a treatment device. As another example, the processing device 120 may determine whether the feature data satisfies a trigger condition. In response to determining that the feature data satisfies the trigger condition, the processing device 120 may generate, based on the feature data, a trigger pulse signal including a trigger delay for acquiring the image data from the time when the trigger pulse signal generates. The processing device 120 may cause the imaging device to scan the subject based at least in part on the trigger pulse signal. As still another example, the processing device 120 may acquire original image data of the subject by the imaging device (e.g., the medical device 110) synchronously with the acquisition of the physiological data by the monitoring device. The processing device 120 may determine the image data from the original image data based on the feature data.

Figure 4A:
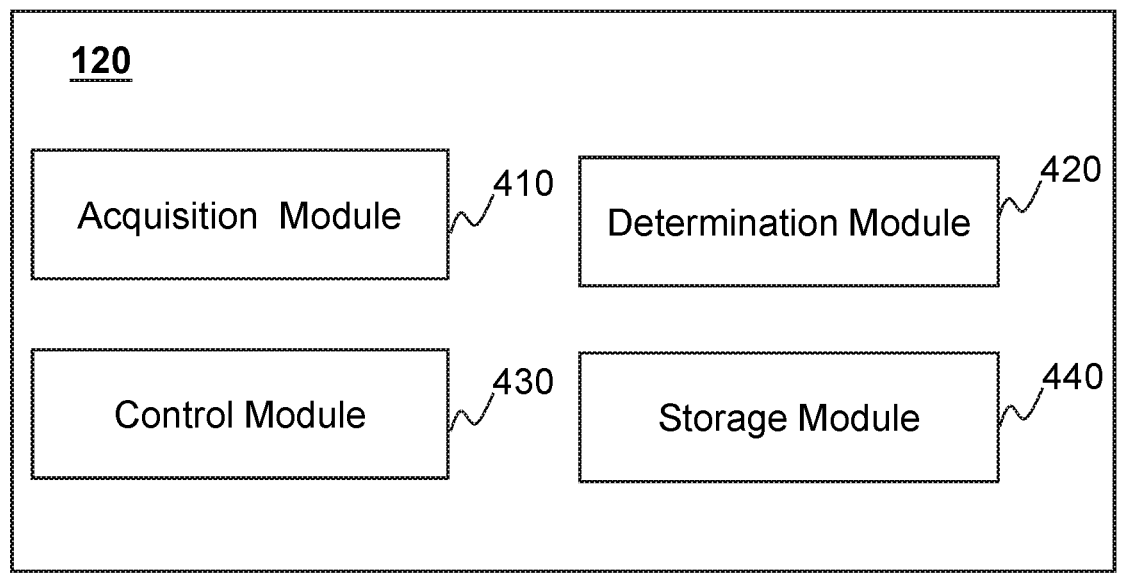
FIG. 4A is a block diagram illustrating an exemplary processing device according to some embodiments of the present disclosure.
Figure 4B:
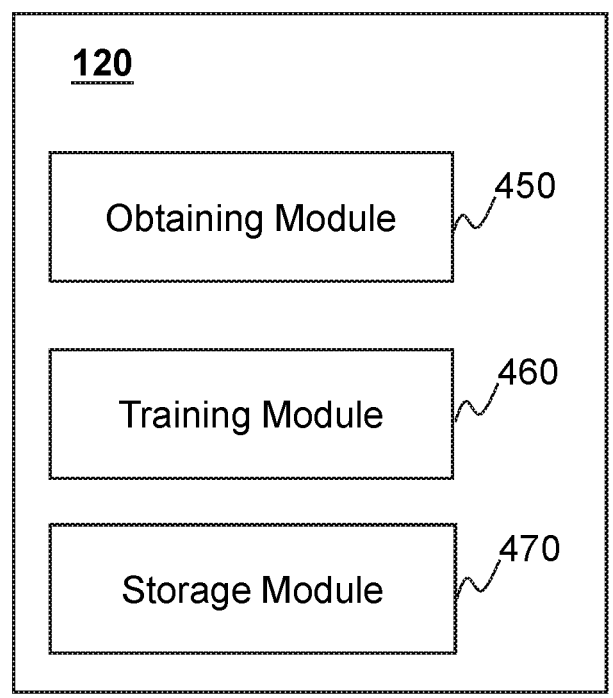
FIG. 4B is a block diagram illustrating an exemplary processing device according to some embodiments of the present disclosure.

In some embodiments, the processing device 120 may determine the trained machine learning model by training a machine learning model using a plurality of training samples obtained from a sample set. The trained machine learning model used in the present disclosure (e.g., the trained machine learning model) may be updated from time to time, e.g., periodically or not, based on a sample set that is at least partially different from the original sample set from which the original trained machine learning model is determined. For instance, the trained machine learning model (e.g., the trained machine learning model) may be updated based on a sample set including new samples that are not in the original sample set. In some embodiments, the determination and/or updating of the trained machine learning model (e.g., the trained machine learning model) may be performed on a processing device, while the application of the trained machine learning model may be performed on a different processing device. For example, the determination and/or updating of the trained machine learning model may be performed by the modules of the processing device as shown in FIG. 4B. The application of the trained machine learning model may be performed by the modules of the processing device as shown in FIG. 4A. In some embodiments, the determination and/or updating of the trained machine learning model (e.g., the trained machine learning model) may be performed on a processing device of a system different than the medical system 100 or a server different than a server including the processing device 120 on which the application of the trained machine learning model is performed. For instance, the determination and/or updating of the trained machine learning model (e.g., the trained machine learning model) may be performed on a first system of a vendor who provides and/or maintains such a machine learning model and/or has access to training samples used to determine and/or update the trained machine learning model, while image generation based on the provided machine learning model may be performed on a second system of a client of the vendor. In some embodiments, the determination and/or updating of the trained machine learning model (e.g., the trained machine learning model) may be performed online in response to a request for image generation. In some embodiments, the determination and/or updating of the trained machine learning model may be performed offline.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical device 110, the terminal(s) 140, and/or the storage device 130 via the network 150. As another example, the processing device 120 may be directly connected to the medical device 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. The data may include image data acquired by the processing device 120, algorithms and/or models for processing the image data, etc. For example, the storage device 130 may store image data (e.g., PET images, PET projection data, etc.) acquired by the medical device 110. As another example, the storage device 130 may store one or more algorithms for processing the image data, a trained machine learning model, etc. In some embodiments, the storage device 130 may store data and/or instructions that the processing device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140, etc.). One or more components in the medical system 100 may access the data or instructions stored in the storage device 130 via the network 150. In some embodiments, the storage device 130 may be directly connected to or communicate with one or more other components in the medical system 100 (e.g., the processing device 120, the terminal(s) 140, etc.). In some embodiments, the storage device 130 may be part of the processing device 120.

The terminal(s) 140 may include a mobile device 141, a tablet computer 142, a laptop computer 143, or the like, or any combination thereof. In some embodiments, the mobile device 141 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the medical system 100. In some embodiments, one or more components of the medical device 110 (e.g., an MRI device, a PET device, etc.), the terminal(s) 140, the processing device 120, the storage device 130, etc., may communicate information and/or data with one or more other components of the medical system 100 via the network 150. For example, the processing device 120 may obtain data from the medical device 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

In some embodiments, the medical system 100 may include a monitoring device (not shown) configured to acquire physiological signals (i.e., physiological data). Exemplary physiological signals may include an electrocardiogram (ECG) signal, an electromyogram (EMG) signal, an electroencephalogram (EEG) signal, a respiratory signal, a pulse signal, or the like, or a combination thereof.

In some embodiment, the monitoring device may be connected to a subject (e.g., patient) via electrodes. The electrodes may acquire the physiological signal of the subject in parallel with the medical device 110. In some embodiments, the electrodes may include an electrocardiograph electrode, a respiratory impedance electrode, a multi-electrode, or the like, or a combination thereof. For example, the electrodes may include at least one electrocardiograph electrode collecting the ECG signal of the subject. As another example, the electrodes may include at least one respiratory impedance electrode collecting the respiratory signal of the subject. In some embodiments, the electrodes may include at least one multi-electrode. The multi-electrode may collect the electrocardiogram ECG signal, the electromyography (EMG) signal, the electroencephalogram (EEG) signal, the respiratory signal, the pulse signal, or the like, or a combination thereof.

In some embodiments, the monitoring device may acquire the physiological signal using a thermistor sensor, an infrared sensor, a photoelectric sensor, a pressure sensor, or the like, or a combination thereof. In some embodiments, the monitoring device may be integrated into the medical device 110.

It should be noted that the above description of the medical system 100 is merely provided for the purposes of illustration, and not intended to limit the scope of the present disclosure. For persons having ordinary skills in the art, multiple variations and modifications may be made under the teachings of the present disclosure. For example, the assembly and/or function of the medical system 100 may be varied or changed according to specific implementation scenarios.

Figure 2:
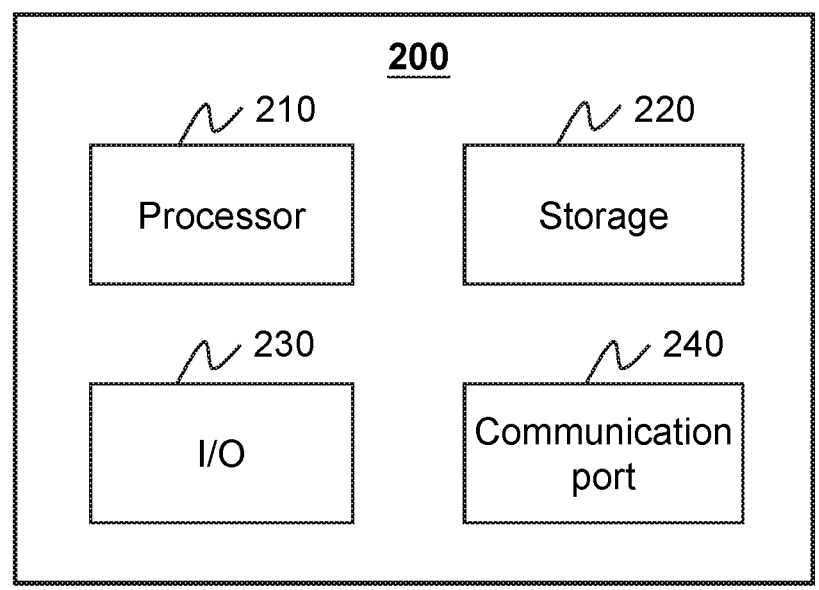
FIG. 2 is a schematic diagram illustrating hardware and/or software components of an exemplary computing device on which the processing device may be implemented according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the medical device 110, the terminal(s) 140, the storage device 130, and/or any other component of the medical system 100. Specifically, the processor 210 may process one or more measured data sets obtained from the medical device 110. For example, the processor 210 may generate an image based on the data set(s). In some embodiments, the generated image may be stored in the storage device 130, the storage 220, etc. In some embodiments, the generated image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuit (ASIC), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal(s) 140, the storage device 130, or any other component of the medical system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
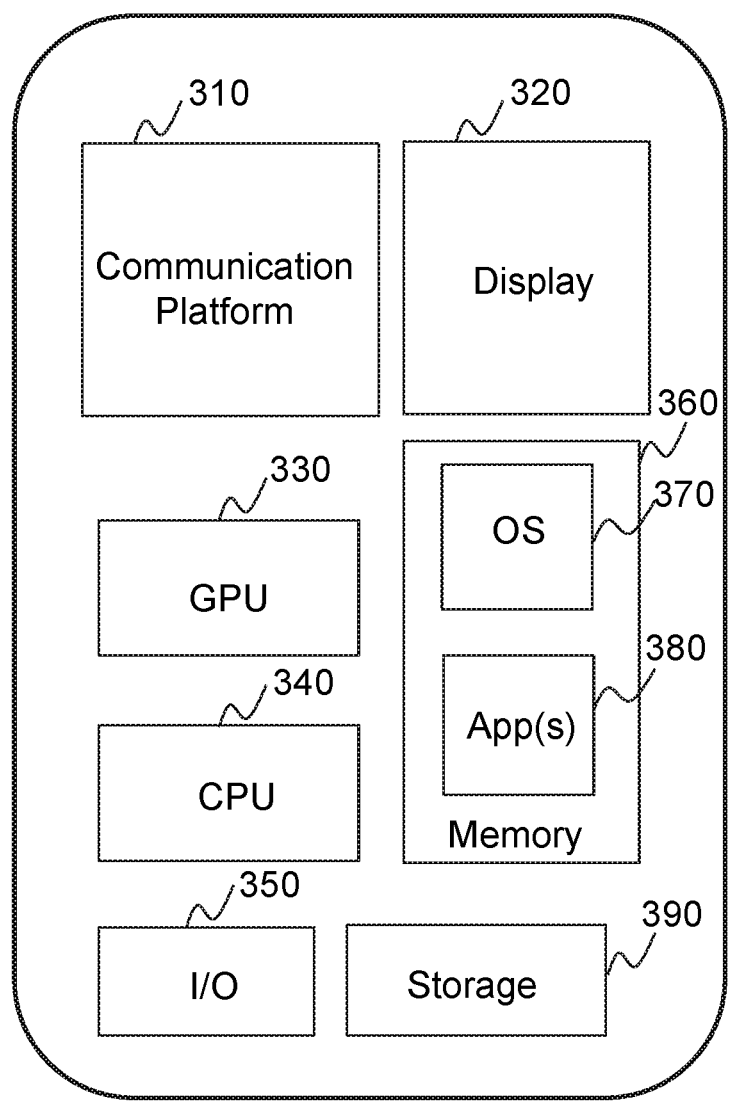
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image data acquisition or other information from the processing device 120. User interactions with the information stream may be achieved via the I/O 350 and provided to the processing device 120 and/or other components of the medical system 100 via the network 150.

To implement various modules, units, and functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies for image data acquisition as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

FIG. 4A is a block diagram illustrating an exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4A, the processing device 120 may include an acquisition module 410, a determination module 420, a control module 430, and a storage module 440. Each of the modules described above may be a hardware circuit that is designed to perform certain actions, e.g., according to a set of instructions stored in one or more storage media, and/or any combination of the hardware circuit and the one or more storage media.

The acquisition module 410 may be configured to acquire physiological data of a subject. The physiological data may correspond to a motion of the subject (e.g., the heart, the abdomen, etc.) over time. In some embodiments, the acquisition module 410 may acquire the physiological data from a storage device, for example, the storage device 130, or any other storage (not shown). In some embodiments, the acquisition module 410 may acquire the physiological data of the subject using a monitoring device. The monitoring device may acquire the physiological data based on an echo signal, an ECG signal, a photoelectric signal, an oscillation signal, a pressure signal, or the like, or a combination thereof. In some embodiments, the acquisition module 410 may acquire the physiological data of the subject using an imaging device (e.g., an MRI device).

The determination module 420 may be configured to determine an output result of a trained machine learning model based on the physiological data. In some embodiments, the determination module 420 may retrieve the trained machine learning model from the storage device 130, the terminal(s) 140, or any other storage device. In some embodiments, the trained machine learning model may be configured to detect feature data from the physiological data. In some embodiments, the trained machine learning model may be configured to determine whether a trigger condition for triggering the imaging device to acquire the image data is satisfied. In some embodiments, the trained machine learning model may be configured to provide a mapping relationship between the physiological data and a gating weighting function based on the detected feature data.

The output result may include the feature data represented in the physiological data, a determination as to whether the trigger condition is satisfied, a determination as to whether the physiological data includes the feature data, the gating weighting function corresponding to the physiological data, or the like, or a combination thereof. In some embodiments, the determination module 420 may input the physiological data into the trained machine learning model. The trained machine learning model may generate the output result using the physiological data. In some embodiments, the determination module 420 may perform a pretreatment operation on the physiological data to obtain preprocessed physiological data and input the preprocessed physiological data into the trained machine learning model. The trained machine learning model may generate the output result using the preprocessed physiological data. The pretreatment operation may include a normalization operation, a denoising operation, a smoothing operation, an downsampling operation, or the like, or a combination thereof.

The control module 430 may be configured to control a medical device to execute a medical procedure, for example, acquire image data of the subject. In some embodiments, if the output result indicates that the trigger condition is satisfied, the control module 430 may generate a trigger pulse signal configured to trigger the medical device (e.g., the medical device 110) to acquire the image data according to an acquisition window and a trigger delay. In some embodiments, the control module 430 may determine whether the trigger condition is satisfied based on the feature data identified by the trained machine learning model. If the feature data satisfies the trigger condition, the trigger pulse signal may be generated to cause the imaging device to scan the subject.

In some embodiments, the control module 430 may cause the imaging device to scan the subject based at least in part on the trigger pulse signal. For example, if one single trigger pulse signal is generated, the control module 430 may cause the imaging device to scan the subject based on the one single trigger pulse signal. As another example, the control module 430 may determine whether a specific count (or number) of multiple trigger pulse signals are generated. In response to determining that the specific count (or number) of consecutive trigger pulse signals are generated, the control module 430 may cause the imaging device (e.g., an MRI device) to scan the subject after a trigger delay from the time the last trigger pulse signal generates.

In some embodiments, the control module 430 may control the image device to acquire original image data of the subject synchronously with the acquisition of the physiological data by the monitoring device. The control module 430 may determine the image data from the original image data based on the output result of the trained machine learning model. For example, the control module 430 may determine the gating weighting function based on the feature data identified from the physiological data or obtain the gating weighting function outputted by the trained machine learning model. The control module 430 may extract the image data from the original data based on the gating weighting function. For example, the control module 430 may extract the image data from the original image data by multiplying the gating weighting function with the original image data.

The storage module 440 may be configured to store data and/or instructions associated with the medical system 100. For example, the storage module 440 may store data of the physiological data of the subject, the trained machine learning model, the feature data, the output result, the trigger pulse signal, etc. In some embodiments, the storage module 440 may be the same as the storage device 130 and/or the storage module 470 in configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the acquisition module 410 and the control module 430 may be integrated into a single module. As another example, some other components/modules may be added into the processing device 120.

FIG. 4B is a block diagram illustrating another exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4B, the processing device 120 may include an obtaining module 450, a training module 460, and a storage module 470. Each of the modules described above may be a hardware circuit that is designed to perform certain actions, e.g., according to a set of instructions stored in one or more storage media, and/or any combination of the hardware circuit and the one or more storage media.

The obtaining module 450 may be configured to obtain data regarding model training, for example, a plurality of training samples. Each of the plurality of training samples may include physiological data of a sample subject. In some embodiments, the plurality of training samples may have the same length of time periods. For example, the length of the time period may be equal to 800 milliseconds.

In some embodiments, each of the plurality of training samples may include annotated physiological data corresponding to the physiological data. The physiological data corresponding to each of the training samples may be annotated by identifying the feature data (e.g., the R wave) from the physiological data. The identification of the feature data may include locating and/or marking the feature data from the physiological data.

In some embodiments, each of the plurality of training samples may include a label corresponding to the physiological data. The physiological data may be used as an input in the training process of a machine learning model, and the label corresponding to the physiological data may be used as a reference output corresponding to the physiological data in the training process of the machine learning model.

In some embodiments, each of the plurality of training samples may include the physiological data and a gating weighting function (or a gating curve) corresponding to the physiological data. The physiological data may be used as input in the training process of a machine learning model, and the gating weighting function corresponding to the physiological data may be used as a reference output corresponding to the physiological data in the training process of the machine learning model.

In some embodiments, the plurality of training samples may include a plurality of positive samples and a plurality of negative samples. Each of the plurality of positive samples may include first physiological data that includes the feature data located at in a specific section of a time period of the first physiological data. Each of the plurality of negative samples may include second physiological data that lacks the feature data located at the specific section of a time period of the second physiological data. In some embodiments, in the plurality of training samples, a count (or number) of the negative samples may exceed the count (or number) of the positive sample, such as 2-3 times the count of the positive samples. In some embodiments, the obtaining module 450 may perform a pretreatment operation on each of at least a portion of the plurality of training samples. The pretreatment operation may include at least one of a normalization operation, a denoising operation, a smoothing operation, or an downsampling operation.

The training module 460 may be configured to generate a trained machine learning model by training a machine learning model using the plurality of training samples in a training process. In some embodiments, the training module 460 may construct the trained machine learning model based on a deep learning model (e.g., a convolutional neural network (CNN) model, a deep belief nets (DBN) machine learning model, a stacked auto-encoder network), a recurrent neural network (RNN) model, a long short term memory (LSTM) network model, a fully convolutional neural network (FCN) model, a generative adversarial network (GAN) model, a back propagation (BP) machine learning model, a radial basis function (RBF) machine learning model, an Elman machine learning model, or the like, or any combination thereof. The training module 460 may train the machine learning model based on the plurality of training samples using a training algorithm. In some embodiments, the training module 460 may perform a plurality of iterations to iteratively update one or more parameter values of the machine learning model to obtain the trained machine learning model. Before the plurality of iterations, the training module 460 may initialize the parameter values of the machine learning model.

The storage module 470 may be configured to store data and/or instructions associated with the medical system 100. For example, the storage module 470 may store data of the plurality of training samples (e.g., the training samples), one or more machine learning models, the trained machine learning model, etc. In some embodiments, the storage module 470 may be the same as the storage device 130 and/or the storage module 440 in configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the obtaining module 450 and the storage module 470 may be integrated into a single module. As another example, some other components/modules may be added into the processing device 120.

Figure 5:
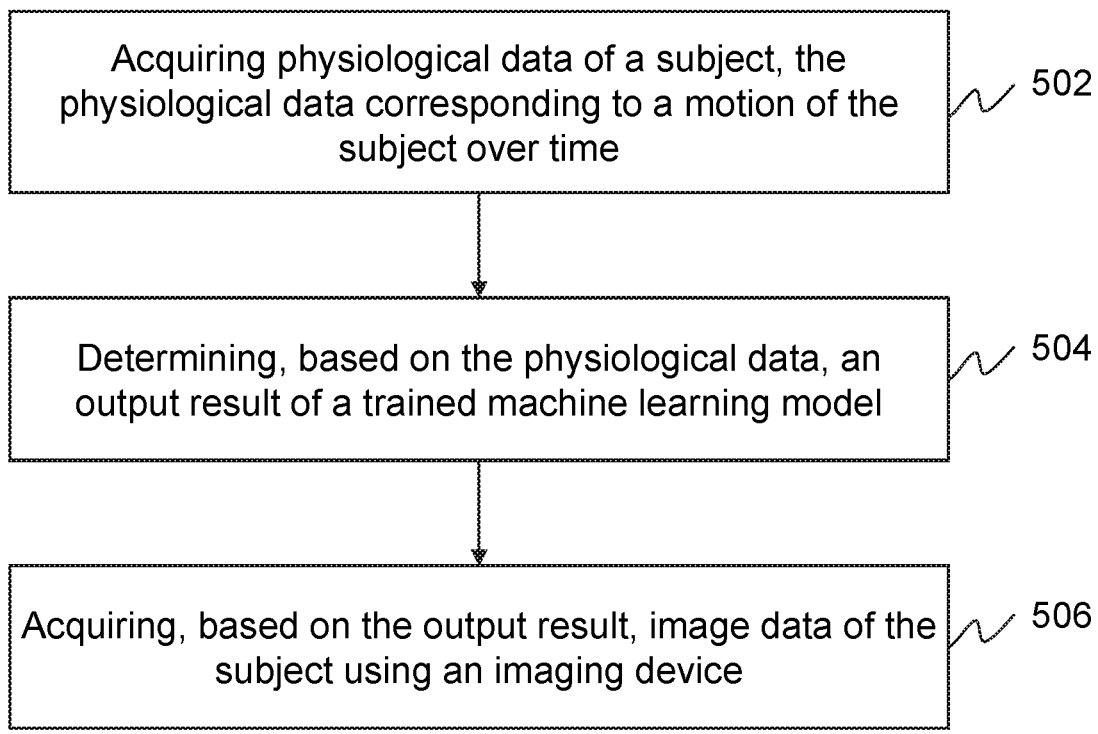
FIG. 5 is a flowchart illustrating an exemplary process for image data acquisition according to some embodiments of the present disclosure.

FIG. 5 is a flowchart illustrating an exemplary process for image data acquisition according to some embodiments of the present disclosure. In some embodiments, process 500 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and described below is not intended to be limiting.

In 502, the processing device 120 (e.g., the acquisition module 410) may acquire physiological data of a subject.

The subject may be biological or non-biological. For example, the subject may include a patient, a man-made object, etc. As another example, the subject may include a specific portion, organ, and/or tissue of the patient. For example, the subject may include the head, the neck, the thorax, the heart, the abdomen, the stomach, the limbs, the pelvic, a blood vessel, soft tissue, a tumor, nodules, or the like, or any combination thereof.

The physiological data may include electrocardiogram (ECG) data, electromyogram (EMG) data, an electroencephalogram (EEG) data, respiration data, pulse data, or the like, or a combination thereof. The physiological data may correspond to a motion of the subject (e.g., the heart, the abdomen, etc.) over time. In other words, the physiological data may contain motion or movement information of the subject. The movement may include incompressible organ deformation (e.g., movement of the liver associated with breathing), compressible organ deformation (e.g., movement of the heart associated with its beating), etc. The movement information may include the movement rate, the movement amplitude or displacement, the movement phase of the subject, etc. For example, the ECG data may represent changes of heart rate or heartbeat amplitude over time.

In some embodiments, the movement phase of the subject may include a resting (or relaxation) phase with a low movement rate or amplitude and a tension phase with a high movement rate or amplitude. For example, the resting (or relaxation) phase associated with the heart may correspond to a diastolic period of the motion of the heart. The tension phase associated with the heart may correspond to a systolic period of the motion of the heart. As another example, the resting (or relaxation) phase associated with the respiratory motion may correspond to an expiratory period. The tension phase associated with the respiratory motion may correspond to an inspiratory phase. According to FIG. 9, the heart performs a periodic movement, including an alternating sequence of a tension phase corresponding to a time period t1 from the peak of an R wave to the end of a T wave, and a resting (or relaxation) phase corresponding to a time period t2 from the end of the T wave to the peak of another R wave generated in the next cycle. More descriptions regarding the ECG data may be found in FIG. 10 and the descriptions thereof.

In some embodiments, the processing device 120 may obtain the physiological data from a storage device, for example, the storage device 130, or any other storage (not shown). For example, a monitoring device may acquire the physiological data of the subject during a time period (e.g., 1 second, 10 seconds, 30 seconds, 1 minute, 3 minutes, 30 minutes, etc.) and store the acquired physiological data in the storage device. The processing device 120 may obtain the physiological data from a storage device. In some embodiments, the processing device 120 may obtain the physiological data from the monitoring device. For example, the monitoring device may acquire the physiological data of the subject during a time period (e.g., 1 second, 800 milliseconds, 50 milliseconds, 1 millisecond, etc.) and transmit the acquired physiological data to the processing device 120. More descriptions for physiological data acquisition may be found elsewhere in the present disclosure (e.g., FIG. 8, and the descriptions thereof).

The monitoring device may be configured to acquire the physiological data of the subject. In some embodiments, the monitoring device may acquire the physiological data based on an echo signal, an ECG signal, a photoelectric signal, an oscillation signal, a pressure signal, or the like, or a combination thereof. In some embodiments, the monitoring device acquiring the physiological data based on the echo signal may also be referred to as a non-contact detector based on an antenna. The non-contact detector may emit an electromagnetic wave to the subject and the subject may generate the echo signal after receives the electromagnetic wave. The non-contact detector may acquire the echo signal and extract the physiological data (e.g., the ECG data or the respiration data) from the echo signal. The non-contact detector may provide beneficial effects including, such as a non-contact acquisition of the physiological data.

In some embodiments, the monitoring device acquiring the physiological data based on the ECG signal may include a chest band electrode detector, an electrocardiogram detector, or the like. For example, the monitoring device acquiring the physiological data based on the ECG signal may detect multiple-lead ECG signals using electrodes. The physiological data acquired by the monitoring device based on the ECG signal may be accurate.

In some embodiments, the monitoring device acquiring the physiological data based on the photoelectric signal may include a monitoring device based on photoelectric transmission, a monitoring device based on photoelectric reflection, or the like. The monitoring device acquiring the physiological data based on the photoelectric signal may emit one or more light beams to the subject and detect the photoelectric signal generated based on a transmitted light or a reflected light after the subject receives the one or more light beams. The monitoring device may convert the photoelectric signal into the physiological data. In some embodiments, the monitoring device may include a sensor (e.g., a photoelectric sensor) configured to generate and emit a light beam and detect the transmitted light or the reflected light. Since blood may absorb light of a particular wavelength, a large amount of the light of the particular wavelength may be absorbed. Therefore, the physiological data (e.g., the ECG data) may be detected by the monitoring device based on the photoelectric signal reflected or transmitted by the subject. It may be convenient to acquire the physiological data using the monitoring device based on the photoelectric signal, and the monitoring device based on the photoelectric signal may be easy to operate.

In some embodiments, the monitoring device acquiring the physiological data based on the oscillation signal may generate the oscillation signal after the monitoring device detects an oscillation caused by the motion of the subject (e.g., an oscillation caused by heartbeat). The monitoring device acquiring the physiological data based on the oscillation signal may include a sensor (e.g., a pressure sensor) that is configured to detect the oscillation. The monitoring device based on the oscillation signal may acquire the physiological data (e.g., the ECG data) by processing and converting the oscillation signal. The monitoring device acquiring the physiological data based on the oscillation signal may be easy to operate.

In some embodiments, the monitoring device acquiring the physiological data based on the pressure signal may generate the pressure signal after the monitoring device detects a pressure change caused by the motion of the subject. The monitoring device acquiring the physiological data based on the pressure signal may include a sensor (e.g., a pulse sensor, a pressure sensor) that is configured to detect the pressure change. The monitoring device based on the pressure signal may acquire the physiological data (e.g., the respiration data, the pulse data) by processing and converting the pressure signal. In some embodiments, the monitoring device based on the pressure signal may include an abdominal band electrode detector. The abdominal band electrode detector may use a pressure sensor to obtain the pressure change on an abdominal band caused by respiration to detect a respiratory movement (e.g., the respiratory data).

In some embodiments, the physiological data of the subject may be acquired by an imaging device. For example, an MRI device may acquire MR signal changes caused by the respiratory movement or the heartbeat through a magnetic resonance navigation sequence (e.g., a navigation echo T2W1 sequence). The processing device 120 may determine the physiological data by analyzing a motion parameter of the subject (e.g., the position of the center of mass) characterized in the change in the MR signal.

In 504, the processing device 120 (e.g., the determination module 420) may determine, based on the physiological data, an output result of a trained machine learning model.

In some embodiments, the processing device 120 may retrieve the trained machine learning model from the storage device 130, the terminals(s) 140, or any other storage device. For example, the trained machine learning model may be determined by training a machine learning model offline based on a plurality of training samples using the processing device 120 or a processing device other than the processing device 120. The trained machine learning model may be stored in the storage device 130, the terminals(s) 140, or any other storage device. The processing device 120 may retrieve the trained machine learning model from the storage device 130, the terminals(s) 140, or any other storage device in response to receipt of a request for image data acquisition. More descriptions regarding the plurality of training samples may be found in FIG. 6. The training process of the trained machine learning model may be performed according to process 600 and process 700.

The trained machine learning model may be configured to detect feature data from the physiological data. As used herein, the detection of the feature data may include determining whether the physiological data includes the feature data and/or identifying (e.g., locate, and/or mark) the feature data from the physiological data (or the preprocessed physiological data). In some embodiments, the trained machine learning model may be further configured to determine whether a trigger condition for triggering the imaging device to acquire the image data is satisfied based on the detected feature data. In some embodiments, the trained machine learning model may be configured to provide a mapping relationship between the physiological data and a gating weighting function based on the detected feature data.

The output result may include the feature data represented in the physiological data, a determination as to whether the trigger condition is satisfied, a determination as to the physiological data includes the feature data, the gating weighting function corresponding to the physiological data, etc.

The feature data may be used to identify a resting (or relaxation) phase and/or a tension phase of the motion of the subject. The feature data may include one or more feature points (e.g., a peak and/or a valley in the physiological data), one or more feature segments (e.g., at least a portion of a wave, e.g., an R wave, a T wave, a P wave, a Q wave, a S wave), etc. For example, the feature data may include position information associated with a peak of an R wave, a rising edge of the R wave, a falling edge of the R wave, the R wave, etc., in the ECG data (e.g., an electrocardiogram) and/or in the respiration data. As another example, the feature data may include position information associated with a peak of a T wave, a rising edge of the T wave, a falling edge of the T wave, the T wave, etc., in the ECG data (e.g., an electrocardiogram). As still another example, the feature data may include at least a portion of each of one or more resting phases (e.g., a diastolic period) and/or at least a portion of each of one or more tension phases (e.g., a systolic period) of the motion of the subject. As still another example, the feature data may include position information associated with a peak of a P wave, a rising edge of the P wave, a falling edge of the P wave, the P wave, etc., in the ECG data (e.g., an electrocardiogram). As used herein, the position information associated with a feature point or feature segment in the physiological data refers to time information when the feature point or feature segment presented in the physiological data.

In some embodiments, the output result may include the time information of the feature data. In some embodiments, the output result may include at least a portion of the physiological data with identified feature data. For example, the trained machine learning model may locate and/or mark the feature data (e.g., the position information associated with at least one of the peak of the R wave, the rising edge of the R wave, or the falling edge of the R wave in the ECG data) in the physiological data. The trained machine learning model may output the physiological data with the marked feature data or output the feature data (e.g., the position information associated with at least one of the peak of the R wave, the rising edge of the R wave, or the falling edge of the R wave in the ECG data). In some embodiments, the feature data may be presented in the form of text, a curve, an image, etc. In some embodiments, the feature data may be marked using a bounding box. The bounding box may enclose feature data (e.g., the R wave) in the training sample. The bounding box may have any shape and/or size. For example, the bounding box may have the shape of a square, a rectangle, a triangle, a polygon, a circle, an ellipse, an irregular shape, or the like. In some embodiments, the feature data may be marked using an arrow, a highlight, a line type or color, or the like, or a combination thereof.

In some embodiments, the output result may indicate whether the physiological data includes the feature data (e.g., at least a portion of an R wave). For example, if the physiological data includes the feature data (e.g., at least a portion of an R wave), the trained machine learning model may generate the output result indicating a truth value (e.g., 1). If the physiological data lacks the feature data (e.g., at least a portion of an R wave), the trained machine learning model may generate the output result indicating a false value (e.g., 0).

In some embodiments, the output result may indicate whether the trigger condition is satisfied. For example, if the trigger condition is satisfied, the trained machine learning model may generate the output result indicating a truth value (e.g., 1). If the trigger condition is unsatisfied, the trained machine learning model may generate the output result indicating a false value (e.g., 0). The trigger condition may indicate that an imaging device (e.g., an MR scanner) may be triggered to scan the subject after a trigger delay from the time when the feature data (e.g., the R wave) is detected in the physiological data.

Figure 10:
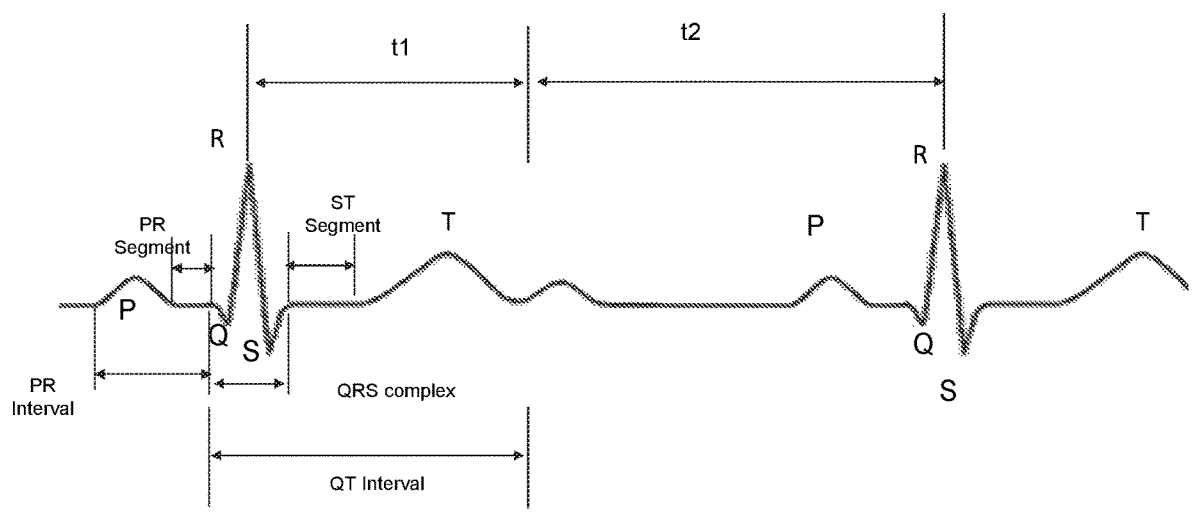
FIG. 10 is a schematic diagram illustrating an exemplary ECG according to some embodiments of the present disclosure.

The gating weighting function may be used to determine a portion of original image data of the subject acquired by an imaging device synchronously with the acquisition of the physiological data by the monitoring device. The gating weighting function may include a plurality of weighting values corresponding to the physiological data. Each of the plurality of weighting values may correspond to a portion of the physiological data acquired at a time or period. The weighting values may be in a range from 0 to 1. For example, if the physiological motion of the subject is significant during the tension phase (e.g., time period t1 as shown in FIG. 10), weighting values corresponding to the tension phase may be relatively small, such as approximate to or equal to 0; if the physiological motion of the subject is mild during the resting phase (e.g., time period t1 as shown in FIG. 10), the weighting values corresponding to the resting phase may be relatively large, such as approximate to or equal to 1.

In some embodiments, the processing device 120 may input the physiological data into the trained machine learning model. The trained machine learning model may generate the output result using the physiological data. In some embodiments, since the physiological data of the subject may include abnormal data and/or noise signals, the processing device 120 may perform a pretreatment operation on the physiological data to obtain preprocessed physiological data. The processing device 120 may input the preprocessed physiological data into the trained machine learning model. The trained machine learning model may generate the output result using the preprocessed physiological data.

In some embodiments, the pretreatment operation may include a normalization operation, a denoising operation, a smoothing operation, an downsampling operation, or the like, or a combination thereof.

In some embodiments, the normalization operation may be used to normalize amplitudes of the physiological data using a normalization algorithm, such as the z-score correction algorithm. For example, the processing device 120 may perform the normalization operation on the physiological data using the z-score correction algorithm according to the following Equation (1):

$$\text{Data}_N = (\text{Data}_O - \text{Data}_M)/Se, \tag{1}$$

where $\text{Data}_N$ refers to normalized physiological data (i.e., the preprocessed physiological data), $\text{Data}_O$ refers to the physiological data obtained in 502, $\text{Data}_M$ refers to a mean of specific physiological data of the subject acquired in a certain time period, and Se refers to a square error of the specific physiological data acquired in the certain time period. The specific physiological data acquired in the certain time period may refer to physiological data acquired in any time period different from the physiological data obtained in 502, for example, physiological data at the beginning of an imaging scanning, physiological data during the imaging scanning, or the like. The mean of the specific physiological data may refer to an average value of amplitudes of the specific physiological data. The square error of the specific physiological data may refer to a square error of the amplitudes of the specific physiological data. The normalized physiological data may fit a standard normal distribution. That is, the mean of the normalized physiological data may be 0, and the standard deviation of the normalized physiological data may be 1. The normalization operation on the physiological data may reduce effects of amplitude differences of physiological data of different subjects, and suppress noise interference.

In some embodiments, the processing device 120 may perform the smoothing operation on the physiological data using a smoothing algorithm, e.g., a 2n+1 points simplex moving average filtering algorithm, a weighting moving average filtering algorithm, a smoothing filtering algorithm using a smooth function, a one dimensional (1D) median filtering algorithm, or the like, or any combination thereof.

In some embodiments, the processing device 120 may perform the downsampling operation on the physiological data using an anti-aliasing filter, which may retain basic features of the physiological data and reducing an amount of physiological data to be processed.

In some embodiments, the processing device 120 may perform the denoising operation on the physiological data using a denoising algorithm, such as using the PauTa criterion (i.e., the 3a criterion), the Chauvenet criterion, a first order difference algorithm, etc. The pretreatment operations may reduce effects of the amplitude differences of physiological data of different subjects, the noises in the physiological data, the abnormal values in the physiological data, etc., on the identification of the feature data. In addition, the pretreatment operation (e.g., the downsampling operation) may decrease data quantity to be processed using the trained machine learning model, thereby reducing the time of identifying the feature data.

In 506, the processing device 120 (e.g., the control module 430) may acquire image data of the subject using an imaging device based on the feature data.

The imaging device may be configured to acquire image data relating to at least one part of a subject. More descriptions regarding the imaging device may be found in FIG. 1 and the descriptions thereof. In some embodiments, if the output result indicates that the trigger condition is satisfied, the processing device 120 may generate a trigger pulse signal configured to trigger the image data to acquire the image data according to an acquisition window and a trigger delay. The length of the acquisition window and the trigger delay may be set by a user or according to a default setting of the medical system 100. The acquisition of the image data based on the physiological data may also be referred to as a gating acquisition technique (such as prospective acquisition).

In some embodiments, the processing device 120 may determine whether the trigger condition is satisfied based on the feature data identified by the trained machine learning model. If the feature data (e.g., the position information associated with at least one of the peak of the R wave, the rising edge of the R wave, or the falling edge of the R wave in the ECG data) satisfies the trigger condition, the trigger pulse signal may be generated to cause the imaging device to scan the subject. More descriptions regarding image data acquisition based on the trigger pulse signal may be found in FIG. 8 and the descriptions thereof.

In some embodiments, the processing device 120 may obtain original image data of the subject acquired by the imaging device synchronously with the acquisition of the physiological data by the monitoring device. The processing device 120 (e.g., the control module 430) may determine the image data from the original image data based on the output result of the trained machine learning model. For example, the processing device 120 may determine the gating weighting function (also referred to as a gating curve) based on the feature data identified from the physiological data or obtain the gating weighting function outputted by the trained machine learning model. The processing device 120 may extract the image data from the original data based on the gating weighting function. For example, the processing device 120 may extract the image data from the original image data by multiplying the gating weighting function with the original image data. The image data may include a portion of the original image data acquired by the imaging device (e.g., the medical device 110 in FIG. 1) at a time when the weighting values are non-zero. Each of the plurality of weighting values may correspond to a time or period. Each of the plurality of weighting values may be multiplied with a portion of the original image data acquired by at a corresponding time or period. Image data acquired at a time or period (e.g., t2 time period as shown in FIG. 10) corresponding to weighting values non-zero may be used for reconstructing an image, while image data acquired at a time or period corresponding to weighting values 0 (e.g., e.g., t1 time period as shown in FIG. 10) may be removed away.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 502 and operation 504 may be combined into a single operation. As another example, one or more other optional operations (e.g., a storing operation) may be added elsewhere in the process 500. In the storing operation, the processing device 120 may store information and/or data (e.g., the physiological data, the feature data, the trained machine learning model, etc.) associated with the medical system 100 in a storage device (e.g., the storage device 130) disclosed elsewhere in the present disclosure.

Figure 6:
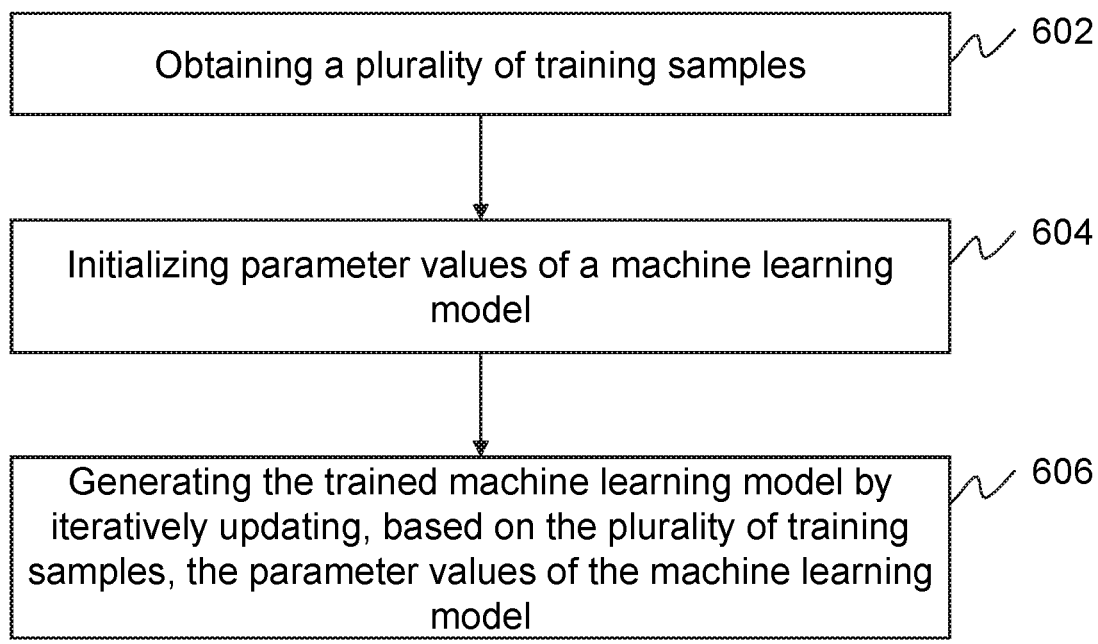
FIG. 6 is a flowchart illustrating an exemplary process for determining a second image based on an iterative process according to some embodiments of the present disclosure.

FIG. 6 is a flowchart illustrating an exemplary process for training a machine learning model according to some embodiments of the present disclosure. In some embodiments, process 600 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, the training process of the trained machine learning model as described in connection with operation 504 in FIG. 5 may be performed according to the process 600.

In 602, the processing device 120 (e.g., the obtaining module 450) may obtain a plurality of training samples. Each of the plurality of training samples may include physiological data of a sample subject. The following descriptions of FIG. 6 are provided with reference to physiological data relating to the cardiac motion unless otherwise stated. It is understood that this is for illustration purposes and not intended to be limiting.

The physiological data may include electrocardiogram (ECG) data, electromyogram (EMG) data, an electroencephalogram (EEG) data, respiration data, pulse data, or the like, or a combination thereof. The sample subjects corresponding to the plurality of training samples may be the same or different. The physiological data may be acquired by a monitoring device during a time period. The time period may be 1.5 seconds, 1 second, 800 milliseconds, 500 milliseconds, etc. More descriptions for the physiological data may be found elsewhere in the present disclosure.

In some embodiments, in order to exclude the influence of lengths of time periods of the training samples on the training of the machine learning model, the plurality of training samples may have the same length of time periods. In some embodiments, if the physiological data includes the ECG data, the length of the time period of the physiological data may be less than or equal to a cardiac cycle. The cardiac cycle of a person may be in a range from 400 milliseconds to 900 milliseconds. In a quiet state, the cardiac cycle may be about 800 milliseconds. For example, the length of the time period may be equal to 800 milliseconds. By limiting the length of the physiological data to less than or equal to the cardiac cycle, at most one position of feature data (e.g., the R wave) may be identified from the same physiological data, which may simplify the training process, improve the accuracy and/or training efficiency of the machine learning model, and/or avoiding an omission of the feature data. In some embodiments, the length of the time period of the physiological data may exceed a cardiac cycle. For example, the length of the time period may be equal to 1000 milliseconds.

In some embodiments, each of the plurality of training samples may include annotated physiological data corresponding to the physiological data. In some embodiments, the physiological data corresponding to each of the training samples may be annotated by identifying the feature data (e.g., the R wave) from the physiological data. The identification of the feature data may include locating and/or marking the feature data from the physiological data. The physiological data may be used as an input in a training process of a machine learning model. The annotated physiological data with marked feature data (i.e., annotated physiological data) may be used as a reference output corresponding to the physiological data in the training process of the machine learning model. The feature data may be identified manually or automatically. For example, the processing device 120 may identify the feature data using an R wave detection algorithm, such as a threshold segment algorithm. The feature data may be marked using a bounding box in the physiological data. The bounding box may enclose feature data (e.g., the R wave) in the physiological data. The bounding box may have any shape and/or size. For example, the bounding box may have the shape of a square, a rectangle, a triangle, a polygon, a circle, an ellipse, an irregular shape, or the like.

In some embodiments, each of the plurality of training samples may include a label corresponding to the physiological data. The physiological data may be used as an input in the training process of a machine learning model. The label corresponding to the physiological data may be used as a reference output corresponding to the physiological data in the training process of the machine learning model. The physiological data corresponding to each of the plurality of training samples may be annotated by the label (i.e., training label) indicating whether the physiological data satisfies a trigger condition (i.e., the trigger condition is satisfied).

The physiological data satisfying the trigger condition means that the current physiological motion of the subject is significant, such as during a tension phase (e.g., time period t1 as shown in FIG. 10), or the physiological motion of the subject transfer from a rest phase to the tension phase. The physiological data not satisfying the trigger condition means that the current physiological motion of the subject is mild, such as during the rest phase. For instance, physiological data not satisfying the trigger condition refers to that the physiological data lack the feature data (e.g., an R wave) located at a specific section of a time period of the physiological data; physiological data satisfying the trigger condition refers to that physiological data includes the feature data located at a specific section of a time period of the physiological data. The specific section of the time period of the physiological data may also be referred to as a trigger window.

If the physiological data satisfies the trigger condition, the physiological data may be a positive training sample. If the physiological data is unsatisfied the trigger condition, the physiological data may be a negative training sample. The label of the physiological data may include a positive label or a negative label. The physiological data may be tagged with a negative label if the physiological data is a negative training sample. The physiological data may be tagged with a positive label if the physiological data is a positive training sample. The physiological data may be tagged with a binary label (e.g., 0 or 1, positive or negative, etc.). For example, a negative training sample may be tagged with a negative label (e.g., "0"), while a positive training sample may be tagged with a positive label (e.g., "1").

The specific section of the time period may be defined from a time point in the time period to an ending time of the time period. In some embodiments, a length of the specific section of the time period may be less than a length of an acquisition window during which an imaging device acquires image data. The acquisition window may be located after the feature data with a trigger delay. The length of the acquisition window of the imaging device may be set by an operator or according to a default setting of the medical system 100. For example, the length of an acquisition window of an imaging device for acquiring image data may be 20 milliseconds, 30 milliseconds, 50 milliseconds, etc. The imaging device may include an MRI device, a PET device, a SPECT device, a PET-CT device, etc., as described elsewhere in the present disclosure (e.g., FIG. 1 and the descriptions thereof). In some embodiments, the length of the specific section of the time period may be in a range between 10 milliseconds and 50 milliseconds, or in a range between 10 and 20 milliseconds, etc. For example, the length of the specific section of the time period may be 10 milliseconds, 15 milliseconds, 20 milliseconds, 25 milliseconds, 30 milliseconds, 35 milliseconds, 40 milliseconds, 45 milliseconds, 50 milliseconds, etc.

In some embodiments, the plurality of training samples may include a plurality of positive samples and a plurality of negative samples. Each of the plurality of positive samples may include first physiological data that includes the feature data located at in a specific section of a time period of the first physiological data, for example, the first physiological data in FIG. 11. More descriptions regarding the first physiological data may be found in FIG. 11 and the descriptions thereof. Each of the plurality of negative samples may include second physiological data that lacks the feature data located at the specific section of a time period of the second physiological data, for example, a second physiological data e in FIG. 12. More descriptions regarding the second physiological data may be found in FIG. 12 and the descriptions thereof. In some embodiments, in the plurality of training samples, a count (or number) of the negative samples may exceed the count (or number) of the positive sample, such as 2-3 times the count of the positive samples. The more negative samples than the positive samples may improve accuracy and F1 score of the trained machine learning model, thereby improving the accuracy of the output result (e.g., the feature data detection) of the trained machine learning model.

In some embodiments, the processing device 120 may perform a pretreatment operation on each of at least a portion of the plurality of training samples. The pretreatment operation may be the same as or different from the pretreatment operation on the physiological data in operation 502. In some embodiments, the pretreatment operation may include at least one of a normalization operation, a denoising operation, a smoothing operation, or an downsampling operation. More descriptions regarding the pretreatment operations may be found in FIG. 5 and the descriptions thereof. The pretreatment operation may improve the efficiency of training the machine learning model.

In some embodiments, each of the plurality of training samples may include the physiological data and a gating weighting function (or a gating curve) corresponding to the physiological data. The physiological data may be used as input in the training process of a machine learning model. The gating weighting function corresponding to the physiological data may be used as a reference output corresponding to the physiological data in the training process of the machine learning model. The gating weighting function may be determined based on the feature data identified from the physiological data. The gating weighting function may include a plurality of weighting values each of which corresponds a portion of the physiological data. The weighting values may be in a range from 0 to 1. For example, if the subject moves dramatically during the tension phase (e.g., QT interval after the R wave as shown in FIG. 10), weighting values corresponding to the tension phase may be relatively small, such as approximate to or equal to 0; if the subject moves gently during the resting phase (e.g., PR interval before the R wave as shown in FIG. 10), the weighting values corresponding to the resting phase may be relatively large, such as approximate to or equal to 1.

In 604, the processing device 120 (e.g., the training module 460) may initialize parameter values of a machine learning model.

In some embodiments, the machine learning model to be trained may include a deep learning model (e.g., a convolutional neural network (CNN) model, a deep belief nets (DBN) machine learning model, a stacked auto-encoder network, etc.), a recurrent neural network (RNN) model, a long short term memory (LSTM) network model, a fully convolutional neural network (FCN) model, a generative adversarial network (GAN) model, a back propagation (BP) machine learning model, a radial basis function (RBF) machine learning model, an Elman machine learning model, or the like, or any combination thereof. In some embodiments, the machine learning model may include a multi-layer structure. For example, the machine learning model may include an input layer, an output layer, and one or more hidden layers between the input layer and the output layer. In some embodiments, the hidden layers may include one or more convolution layers, one or more rectified-linear unit layers (ReLU layers), one or more pooling layers, one or more fully connected layers, or the like, or any combination thereof. As used herein, a layer of a model may refer to an algorithm or a function for processing input data of the layer. Different layers may perform different kinds of processing on their respective input. A successive layer may use output data from a previous layer of the successive layer as input data. In some embodiments, the convolutional layer may include a plurality of kernels, which may be used to extract a feature. In some embodiments, each kernel of the plurality of kernels may filter a portion (i.e., a region). The pooling layer may take an output of the convolutional layer as an input. The pooling layer may include a plurality of pooling nodes, which may be used to sample the output of the convolutional layer, so as to reduce the computational load of data processing and accelerate the speed of data processing speed. In some embodiments, the size of the matrix representing the inputted data may be reduced in the pooling layer. The fully connected layer may include a plurality of neurons. The neurons may be connected to the pooling nodes in the pooling layer. In the fully connected layer, a plurality of vectors corresponding to the plurality of pooling nodes may be determined based on a training sample, and a plurality of weighting coefficients may be assigned to the plurality of vectors. The output layer may determine an output based on the vectors and the weighting coefficients obtained from the fully connected layer.

In some embodiments, each of the layers may include one or more nodes. In some embodiments, each node may be connected to one or more nodes in a previous layer. The number of nodes in each layer may be the same or different. In some embodiments, each node may correspond to an activation function. As used herein, an activation function of a node may define an output of the node given input or a set of inputs. In some embodiments, each connection between two of the plurality of nodes in the initial machine learning model may transmit a signal from one node to another node. In some embodiments, each connection may correspond to a weight. As used herein, a weight corresponding to a connection may be used to increase or decrease the strength or impact of the signal at the connection.

The machine learning model may include a plurality of parameters, such as architecture parameters, learning parameters, etc. Exemplary architecture parameters of the machine learning model may include the size of a kernel of a layer, the total count (or number) of layers, the count (or number) of nodes in each layer, a learning rate, a batch size, an epoch, etc. Exemplary learning parameters may include a connected weight between two connected nodes, a bias vector relating to a node, etc.). Before the training, the machine learning model may have one or more initial parameter values. In the training of the machine learning model, learning parameters of the machine learning model may be updated. Before the updating process, values of the learning parameters of the machine learning model may be initialized. For example, the connected weights and/or the bias vector of nodes of the initial machine learning model may be initialized by assigning random values in a range, e.g., the range from −1 to 1. As another example, all the connected weights of the initial machine learning model may be assigned the same value in the range from −1 to 1, for example, 0. As still an example, the bias vector of nodes in the initial machine learning model may be initialized by assigning random values in a range from 0 to 1. In some embodiments, the parameters of the initial machine learning model may be initialized based on a Gaussian random algorithm, a Xavier algorithm, etc. More descriptions regarding the convolutional neural network (CNN) model may be found in FIG. 9 and the descriptions thereof.

In 606, the processing device 120 (e.g., the training module 460) may generate the trained machine learning model by iteratively updating, based on the plurality of training samples, the parameter values of the machine learning model.

In the training of the machine learning model, the processing device 120 may iteratively update the parameter value(s) of the machine learning model based on the plurality of training samples. The updating of the learning parameters of the machine learning model may be also referred to as updating the machine learning model. For example, the processing device 120 may update the model parameter(s) of the machine learning model by performing one or more iterations until a termination condition is satisfied, wherein at least one of the iteration(s) may include one or more operations of process 700 as described in connection with FIG. 7.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 604 and operation 606 may be combined into a single operation. As another example, one or more other optional operations (e.g., a storing operation) may be added elsewhere in the process 600. In the storing operation, the processing device 120 may store information and/or data (e.g., parameter values, etc.) associated with the training of the machine learning model in a storage device (e.g., the storage device 130) disclosed elsewhere in the present disclosure.

Figure 7:
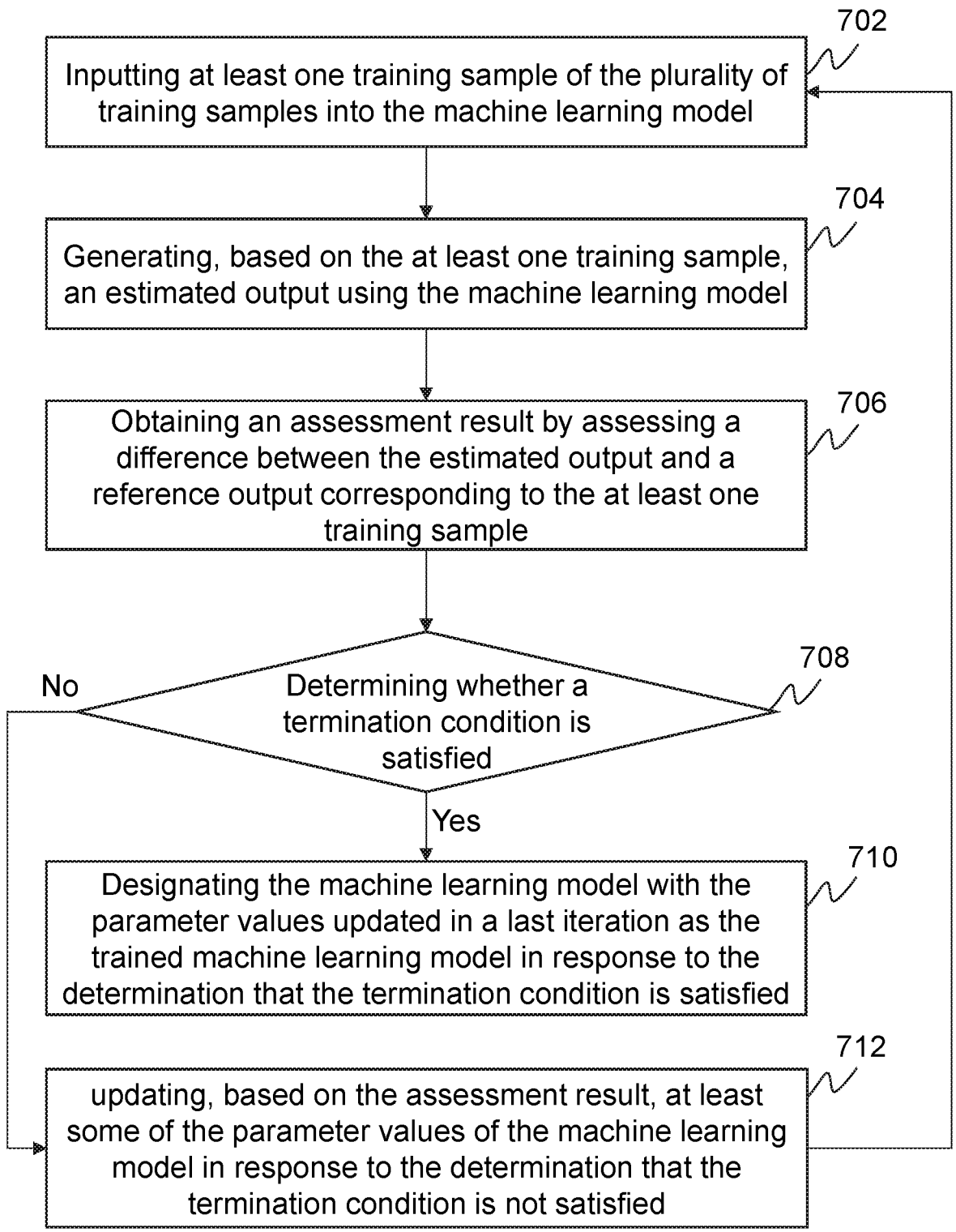
FIG. 7 is a flowchart illustrating an exemplary training process of a trained machine learning model according to some embodiments of the present disclosure.

FIG. 7 is a flowchart illustrating an exemplary training process of a trained machine learning model according to some embodiments of the present disclosure. In some embodiments, process 700 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, the training process of the trained machine learning model as described in connection with operation 606 in FIG. 6 may be performed according to the process 700. For illustration purposes, a current iteration of the iteration(s) is described in the following description. The current iteration may include one or more operations of the process 700.

In 702, the processing device 120 (e.g., the obtaining module 450) may input at least one training sample of the plurality of training samples into a machine learning model. Each of the plurality of training samples may include an input (i.e., physiological data) and a reference output (e.g., annotated physiological data) in the training process of the machine learning model. For example, the reference output may include the annotated physiological data with identified feature data. As another example, the reference output may include a label (a positive label "1" or a negative label "0") indicating whether the physiological data satisfies a trigger condition, i.e., whether the physiological data includes feature data that is located at a specific section of a time period of the physiological data. As still another example, the reference output may include a gating curve corresponding to the physiological data. More descriptions regarding the plurality of training samples and the machine learning model may be found in FIG. 6 and the descriptions thereof. For example, parameter values of the machine learning model may be initialized.

In 704, the processing device 120 (e.g., the training module 460) may generate, based on the at least one training sample, an estimated output using the machine learning model. The machine learning model may generate the estimated output by processing the inputted physiological data based on the reference output.

In some embodiments, if the reference output indicates that the physiological data is a positive sample or a negative sample, the estimated output may indicate that the physiological data is a positive sample or a negative sample. In other words, the estimated output may indicate whether the physiological data satisfies the trigger condition. For example, the estimated output may include a probability that the physiological data satisfies the trigger condition or the physiological data includes feature data that is located at the specific section of the time period of the physiological data.

In some embodiments, if the reference output includes the annotated physiological data with identified feature data, the estimated output may include the physiological data with estimated feature data. For example, the estimated output may include at least a portion of the physiological data with estimated position information associated with at least one of a peak of an R wave, a rising edge of the R wave, or a falling edge of the R wave in the physiological data (e.g., ECG data).

In some embodiments, if the reference output includes a gating weighting function determined based on the feature data identified from the physiological data, the estimated output may include an estimated gating weighting function. More descriptions regarding the feature data may be found in FIG. 5 and the descriptions thereof.

In 706, the processing device 120 (e.g., the training module 460) may obtain an assessment result by assessing a difference between the estimated output and a reference output corresponding to the at least one training sample.

In some embodiments, the assessment result may be a value of a cost function relating to the difference between the estimated output and the reference output. For example, the processing device 120 (e.g., the training module 460) may determine the value of the cost function relating to the difference between the estimated output and the reference output. As used herein, the cost function (or loss function) may refer to a function that measures a difference between the estimated output of the machine learning model and the reference output (i.e., an actual output), wherein the difference may indicate the accuracy of the machine learning model. In some embodiments, the cost function may include a Softmax cross entropy loss function or a square error loss function.

In 708, the processing device 120 (e.g., the training module 460) may determine whether a termination condition is satisfied. The termination condition may provide an indication of whether the machine learning model is sufficiently trained. The termination condition may relate to a cost function or an iteration count of the training process. For example, the processing device 120 may determine a loss function of the machine learning model and determine a value of the cost function based on the difference between the estimated output and the actual output or desired output (i.e., reference output). Further, the processing device 120 may determine the termination condition is satisfied if the value of the loss function is less than a threshold. The threshold may be default settings of the medical system 100 or may be adjustable under different situations. As another example, the termination condition may be satisfied if the value of the cost function converges. The convergence may be deemed to have occurred if the variation of the values of the cost function in two or more consecutive iterations is smaller than a threshold (e.g., a constant). As still another example, the processing device 120 may determine the termination condition is satisfied if a specified number (or count) of iterations are performed in the training process.

In response to a determination that the termination condition is satisfied, the processing device 120 may proceed to operation 710. In 710, the processing device 120 may designate the machine learning model with the parameter values updated in the last iteration as the trained machine learning model (e.g., a trained machine learning model). On the other hand, in response to a determination that the termination condition is not satisfied, the processing device 120 may proceed to operation 712. In 712, the processing device 120 may update at least some of the parameter values of the machine learning model based on the assessment result. For example, the processing device 120 may update the value(s) of the learning parameter(s) of the machine learning model based on the value of the loss function according to, for example, a backpropagation algorithm.

After 712, the processing device 120 may proceed to operation 702 to perform the next iteration until the termination condition is satisfied. In the next iteration, the processing device 120 may obtain multiple groups of training samples in another batch. The size of the batch may refer to a group count or number of the multiple groups of training samples. After the termination condition is satisfied in a certain iteration, the machine learning model in the certain iteration having the updated value(s) of the learning parameter(s) may be designated as the trained machine learning model (e.g., the trained machine learning model).

In some embodiments, after 710, the processing device 120 may test the trained machine learning model by inputting at least one of a plurality of testing samples. The testing sample may be a plurality of physiological data. In some embodiments, the testing sample may be processed in the same manner as the training samples. For example, the testing sample may include a plurality of positive samples and a plurality of negative samples. As another example, in the plurality of testing samples, a count of the negative samples may be 2-3 times a count of the positive samples. As still another example, the plurality of testing samples may be preprocessed as described in operations 502 and 602. However, the physiological data of the testing sample may be different with the physiological data of the training sample. Hence, test results may be ensured accuracy, which may avoid reducing application of the machine learning model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added elsewhere in the process 700. In the storing operation, the processing device 120 may store information and/or data (e.g., a training sample, the trained machine learning model, etc.) associated with the medical system 100 in a storage device (e.g., the storage device 130) disclosed elsewhere in the present disclosure.

Figure 8:
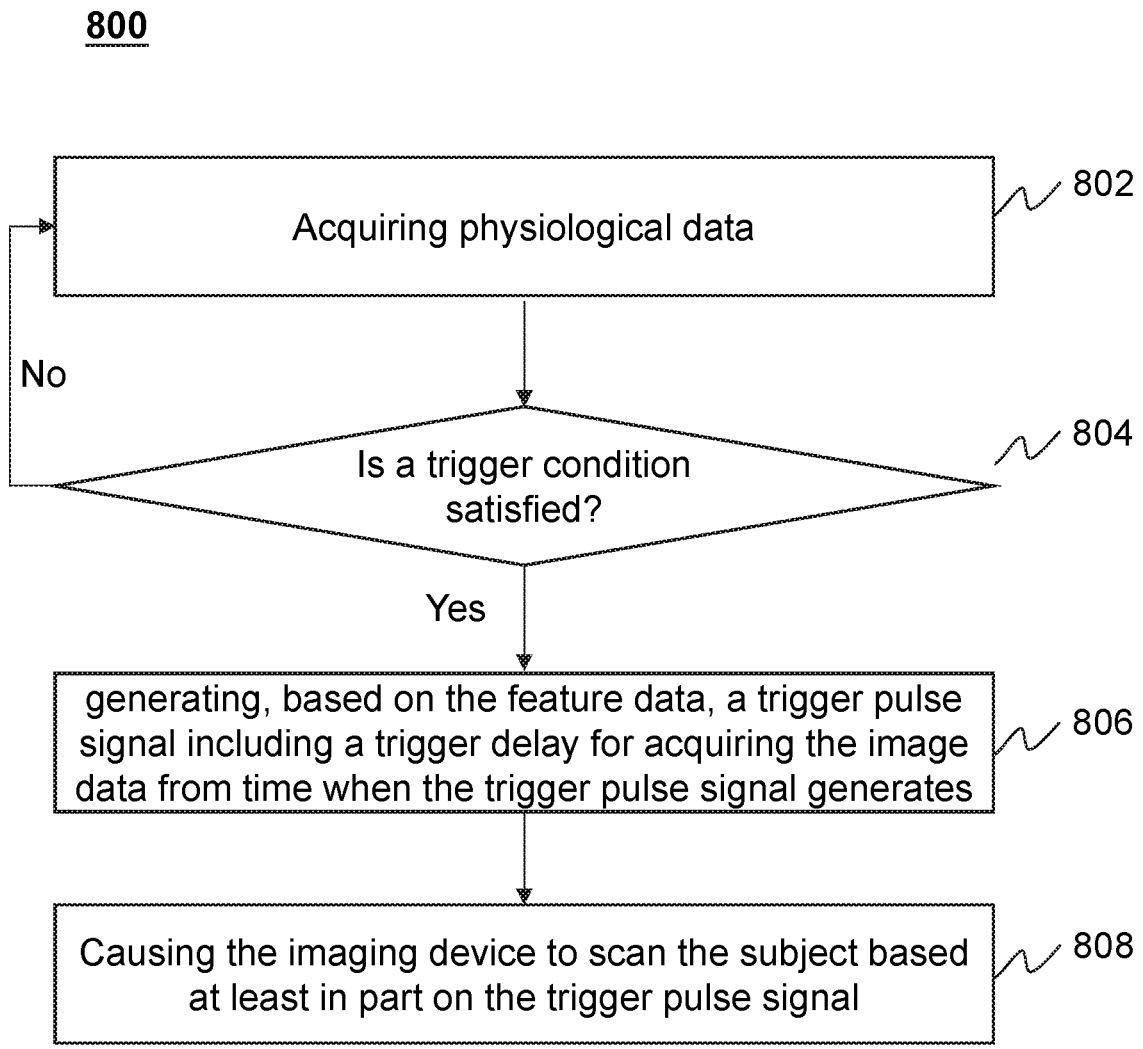
FIG. 8 is a flowchart illustrating an exemplary process for image data acquisition according to some embodiments of the present disclosure.

FIG. 8 is a flowchart illustrating an exemplary process for image data acquisition according to some embodiments of the present disclosure. In some embodiments, process 800 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, one or more operations of the process 800 may be performed to achieve at least part of operation 506 as described in connection with FIG. 5.

In 802, the processing device 120 (e.g., the control module 430) may acquire physiological data. More descriptions for the physiological data may be found elsewhere in the present disclosure (e.g., FIG. 5 and the descriptions thereof).

Figure 13A:
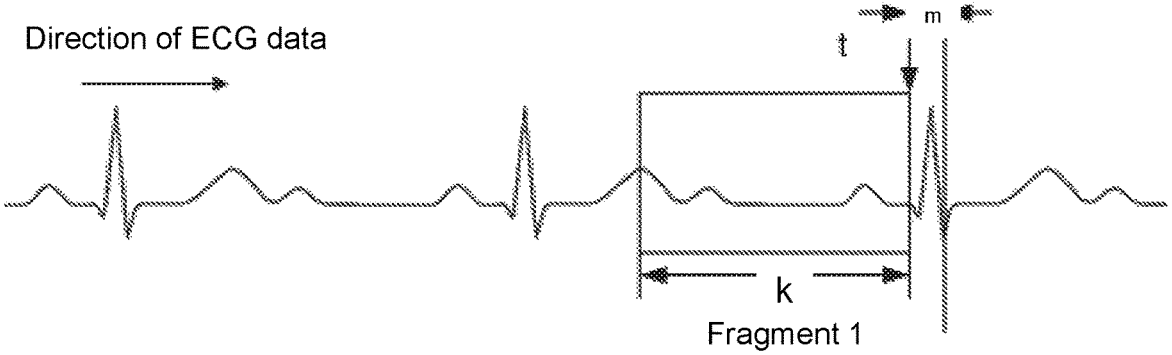
FIGS. 13A-13C are schematic diagrams illustrating an exemplary process for physiological data acquisition according to some embodiments of the present disclosure.
Figure 13B:
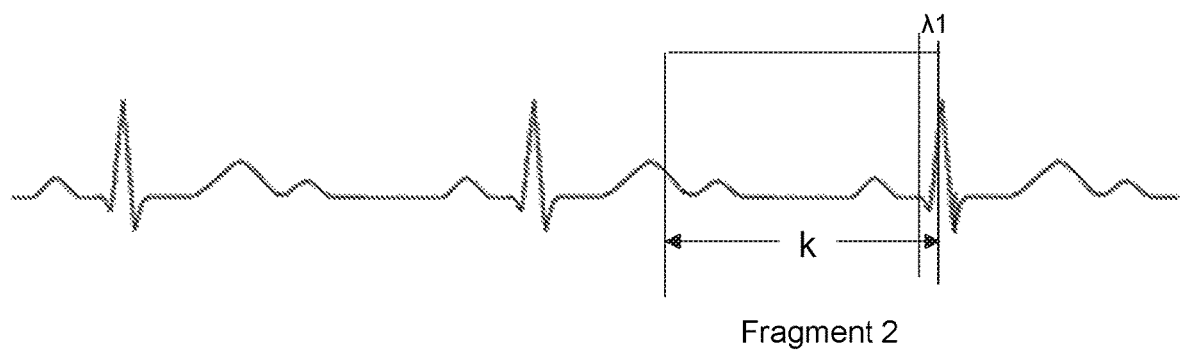
Figure 13C:
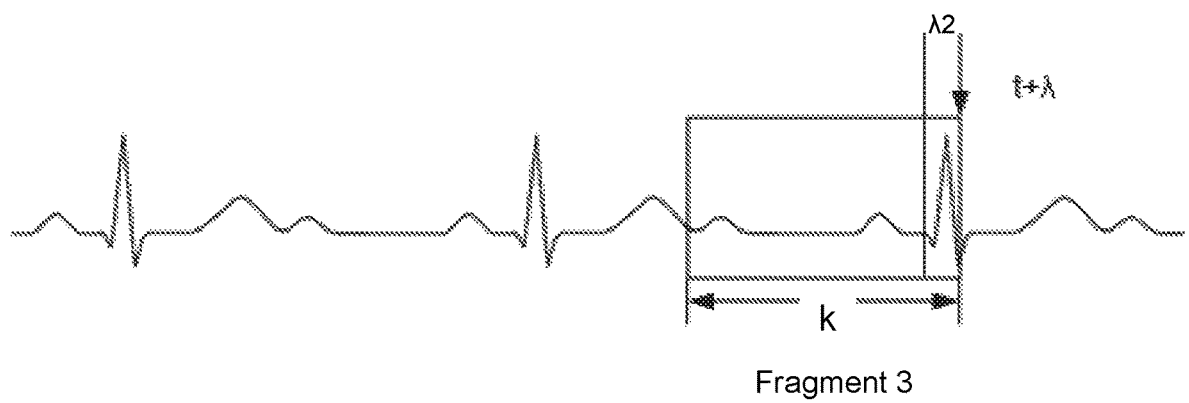

In some embodiments, the physiological data may be obtained by extracting data acquired over time by a monitoring device using a sliding window with width k and step length A. The physiological data may also be referred to as an extracted fragment (e.g., fragment 1, fragment 2, fragment 3 as shown in FIGS. 13A-13C). The width of the sliding window may be equal to the length of the physiological data (i.e., each extracted fragment). In some embodiments, the step length A may be a sampling period of the monitoring device. In some embodiments, the step length A may be less than or equal to a length of the time period of the feature data (e.g., R wave) of the physiological data. For example, as shown in FIG. 13B, the step length A1 may be less than the length of the time period m of the R wave in the ECG data. As shown in FIG. 13C, the step length A2 may be equal to the length of the time period m of the R wave in the ECG data. In some embodiments, the step length A may exceed the length of the time period of the feature data (e.g., R wave) of the physiological data. For example, the step length A may be equal to 10 milliseconds, 20 milliseconds, etc. Two adjacent extracted fragments may have same physiological data when the step length A is less than a length of the time period of each extracted fragment.

In 804, the processing device 120 (e.g., the control module 430) may determine whether a trigger condition is satisfied based on the physiological data (e.g., fragment 1 shown in FIG. 13). In response to a determination that the trigger condition is satisfied, the process 800 may proceed to perform operation 806. In response to a determination that the trigger condition is unsatisfied, the process 800 may return to perform operation 802. The processing device 120 may obtain another physiological data (e.g., fragment 2 shown in FIG. 13).

In some embodiments, the processing device 120 may identify feature data from the physiological data using a trained machine learning model as described elsewhere in the present disclosure. The processing device 120 may determine whether the trigger condition is satisfied based on the feature data. For example, the processing device 120 may input the physiological data into the trained machine learning model and the trained machine learning model may output the physiological data with the identified feature data or without the feature data. The processing device 120 may determine whether the feature data is located at a specific section of the time period of the physiological data. In response to a determination that the feature data is located at the specific section of the time period of the physiological data (e.g., fragment 2 shown in FIG. 13), the processing device 120 may determine that the trigger condition is satisfied. In response to a determination that the physiological data (e.g., fragment 1 shown in FIG. 13) lacks the feature data that is located at the specific section of the time period of the physiological data, the processing device 120 may determine that the trigger condition is not satisfied.

The specific section of the time period of the physiological data may be defined from a time point in the time period to an ending time of the time period of the physiological data. In some embodiments, a length of the specific section of the time period may be less than a length of an acquisition window during which an imaging device acquires image data. For example, the length of the specific section of the time period may be 20 milliseconds, 15 milliseconds, 10 milliseconds, etc. In some embodiments, the length of the specific section of the time period may be equal to or exceed the size length of the sliding window. As a further example, if the feature data is present at the end of 10 milliseconds of the time period of the physiological data, the processing device 120 may determine that the trigger condition is satisfied. The feature data may include position information associated with a peak of an R wave, a rising edge of the R wave, and a falling edge of the R wave in the ECG data, etc.

In some embodiments, the processing device 120 may determine whether the trigger condition is satisfied using the trained machine learning model as described elsewhere in the present disclosure. For example, the processing device 120 may input the physiological data into the trained machine learning model. The trained machine learning model may output a result indicating whether the trigger condition is satisfied.

In 806, the processing device 120 (e.g., the control module 430) may generate a trigger pulse signal based on the feature data, in response to determining that the trigger condition is satisfied. The trigger pulse signal may be configured to cause the imaging device to scan the subject. In some embodiments, the trigger pulse signal may include a trigger delay for acquiring the image data from a reference time point. The reference time point may be when the feature data is detected, when the preceding pulse is applied, when the trigger pulse signal generates, etc. For example, the trigger delay may be 20 milliseconds.

In 808, the processing device 120 (e.g., the control module 430) may cause the imaging device to scan the subject based at least in part on the trigger pulse signal. The imaging device may be configured to acquire image data relating to at least one part of a subject. More descriptions regarding the imaging device may be found in FIG. 1 and the descriptions thereof. In some embodiments, if one single trigger pulse signal is generated, the processing device 120 (e.g., the control module 430) may cause the imaging device to scan the subject based on the one single trigger pulse signal. For example, the processing device 120 (e.g., the control module 430) may cause an MRI device to scan the subject after a trigger delay from the time the one single trigger pulse generates.

In some embodiments, the processing device 120 (e.g., the control module 430) may determine whether a specific count (or number) of multiple trigger pulse signals are generated. In response to determining that the specific count (or number) of consecutive trigger pulse signals are generated, the processing device 120 (e.g., the control module 430) may cause the imaging device (e.g., an MRI device) to scan the subject after a trigger delay from the time the last trigger pulse signal generates. For example, along the data acquisition of the monitoring device, the sliding window may slide to obtain multiple extracted fragments with the step length. Each extracted fragment acquired by the sliding window may be inputted into the trained machine learning model to obtain an output result and the output result may be arranged in chronological order. Further, if the trigger condition is satisfied, the trained machine learning model may output a true value. If the trigger condition is unsatisfied, the trained machine learning model may output a false value. The output values (i.e., true values and/or false values) of the trained machine learning model may eventually cause trigger pulse signals generation to form a pulse signal waveform with a sampling period of the step length of the sliding window. Each trigger pulse signal in the pulse signal waveform may represent at least a portion of the feature data. In some embodiments, the pulse signal waveform may include information about scanning parameters (e.g., scanning time, frequency, or the like, or any combination thereof).

In some embodiments, the step length (e.g., 2 milliseconds) of the sliding window may be less than the length of the time period (e.g., 10 milliseconds) of the feature data (e.g., an R wave). As shown in FIG. 13B, the step length A1 is less than the length of the time period m of the R wave in the ECG data. The trained machine learning models may output several consecutive truth values until an extracted fragment inputted into the trained machine learning model includes the entire feature data (e.g., an R wave). The processing device 120 may cause the imaging device to acquire the image data until determining that the specific count (or number) of consecutive truth values are generated.

For example, when the step length of the sliding window is 1 millisecond and the length of the specific section of the time period of the physiological data is 10 milliseconds that is equal to the length of the time period of the feature data, at least 10 extracted fragments may include at least a portion of the feature data (e.g., an R wave). Each of the 10 extracted fragments may be inputted into the trained machine learning model. The trained machine learning model may continuously detect at least a portion of the feature data for 10 times each of which corresponds to one of the 10 extracted fragments. In other words, the trained machine learning models may output 10 consecutive truth values. The processing device 120 may cause the imaging device to scan the subject until the 10 consecutive truth values are outputted by the trained machine learning model. Accordingly, the imaging device (e.g., an MRI device) may be caused to acquire the image data until the feature data is detected continuously for multiple (e.g., 3) times, which may greatly reduce the probability of detection error of the feature data using the trained machine learning model.

In addition, since only one scan is performed during a cardiac cycle (about 800 milliseconds), in response to a determination that the trigger condition is satisfied, the processing device 120 may further determine whether a difference between a time when the last extracted fragment (e.g., fragment 1 as shown in FIG. 13A) is acquired and a current time when a current extracted fragment (e.g., fragment 2 as shown in FIG. 13B fragment 3 as shown in FIG. 13C) is acquired exceeds a threshold (e.g., 100 milliseconds). In response to determining that the difference between the time when the last extracted fragment is acquired and the current time when the current extracted fragment acquired exceeds the threshold (e.g., 100 milliseconds), the processing device 120 may trigger the imaging device to acquire the image data, which may avoid to repeatedly perform scans during a cardiac cycle. The threshold may be greater than the length of the acquisition window but less than the cardiac cycle, such as 100 milliseconds.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., a storing operation) may be added elsewhere in the process 800. In the storing operation, the processing device 120 may store information and/or data (e.g., a training sample, the trained machine learning model, etc.) associated with the medical system 100 in a storage device (e.g., the storage device 130) disclosed elsewhere in the present disclosure.

Figure 9:
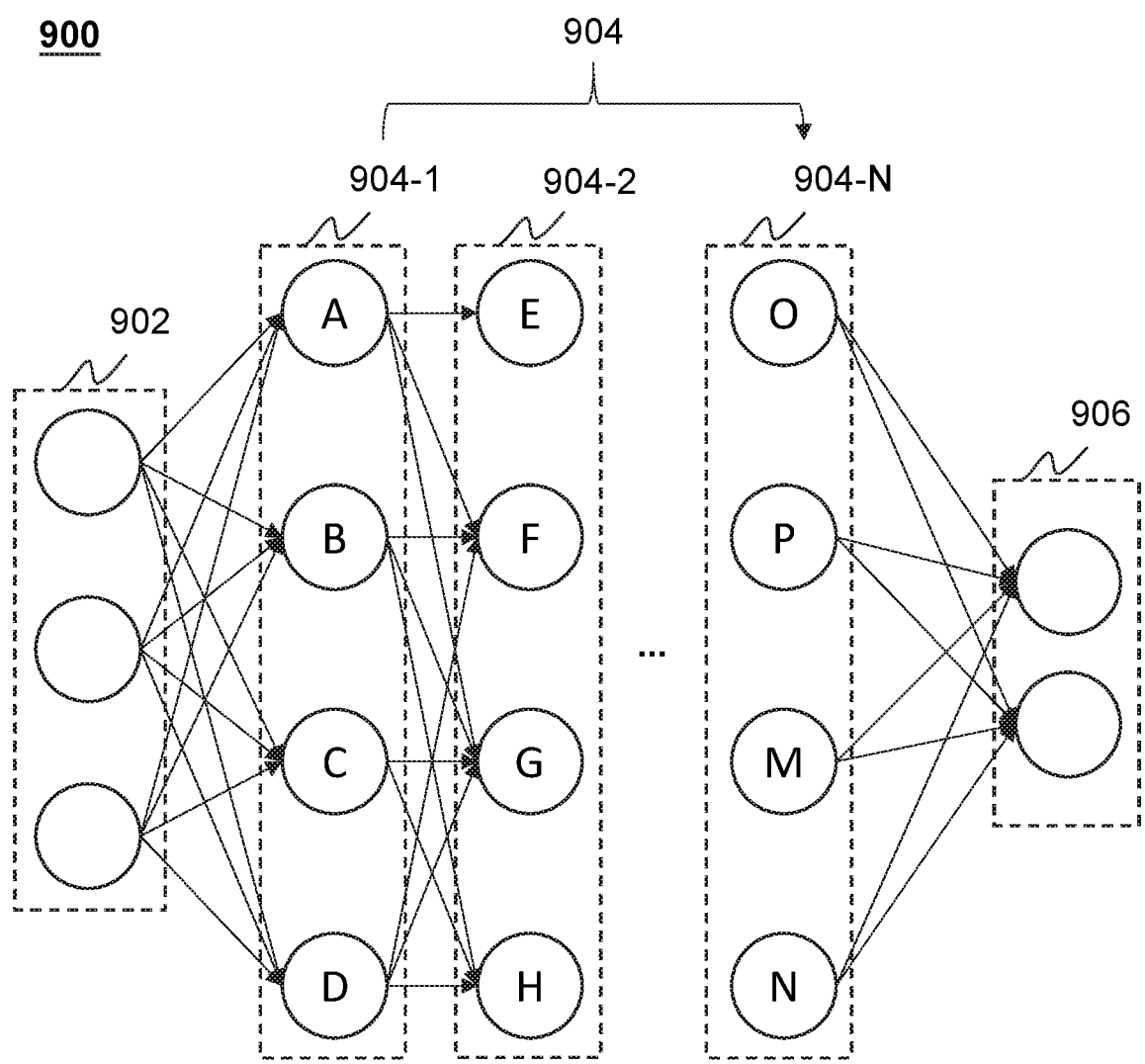
FIG. 9 is a schematic diagram illustrating an exemplary CNN model according to some embodiments of the present disclosure.

FIG. 9 is a schematic diagram illustrating an exemplary CNN model 900 according to some embodiments of the present disclosure. In some embodiments, the CNN model 900 may be a component of a trained machine learning model as described elsewhere in this disclosure (e.g., FIGS. 5-7 and the relevant descriptions).

The machine learning model in the embodiment may include any artificial neural network that may realize a deep learning algorithm. The artificial neural networks may be proven and successfully implemented in data prediction related applications, such as data trend prediction, speech recognition, or the like. In the artificial Neural Networks, Convolutional Neural Networks (CNN for short) may be a kind of Feedforward Neural Networks with convolution computation and depth structure. The CNN model may be one of the representative algorithms of deep learning algorithms. The CNN models may have the ability of representational learning and translate input information without changing the classification according to the hierarchical structure.

The artificial neural network may have the characteristics of memory, parameter sharing, and Turing completeness. Hence, the artificial neural network may have advantages in learning the nonlinear characteristics of sequence data. Physiological data (e.g., electrocardiogram (ECG) data, respiration data, or the like) may have strong regularity and coherence, which is a typical sequence data. Therefore, in the embodiment, the artificial neural network may be used to learn the physiological data and determine feature data.

In the embodiment, the architecture of a neural network may be implemented by tensorflow. As shown in FIG. 9, the CNN model 900 may include an input layer 902, a plurality of hidden layers 904, and an output layer 906. The hidden layers 904 may include one or more convolutional layers, one or more rectified linear unit (ReLU) layers, one or more pooling layers, one or more fully connected layer, or the like, or any combination thereof. For illustration purposes, exemplary hidden layers 904, including a convolutional layer 904-1, a pooling layer 904-2, and a fully connected layer 904-N, are provided in FIG. 9.

The input layer 902 may be used for data input. For example, the input data may be physiological data in the process of application of the CNN model 900. As another example, the input data may be a training sample in the process of training. Since the physiological data is waveform data without color information, the input of the CNN model 900 may be two-dimensional data.

The convolutional layer 904-1 may include a plurality of kernels (e.g., A, B, C, and D), which may be used to extract a feature of the physiological data. The physiological data may be inputted into the convolutional layer 904-1 in the form of an image. In some embodiments, each kernel of the plurality of kernels may filter a portion of the image (e.g., an ECG) to generate a specific image feature corresponding to the portion. The specific image feature may be determined based on the kernels. Exemplary image features may include a low-level feature (e.g., an edge feature, a textural feature), a high-level feature, or a complicated feature. As used herein, the low-level feature (e.g., an edge feature, a textural feature) may be extracted by a low convolution layer, while the more layered network may iteratively extract more complex features (e.g., the high-level feature, the complicated feature) from low-level features.

In some embodiments, a normalization layer may be present (not shown) in the CNN model. The normalization layer may be used to force an input distribution which gradually maps to a nonlinear function and then to a limit saturation region of a value interval to return to a standard normal distribution with a mean value of 0 and a variance of 1. Therefore, the input value of the nonlinear transformation function may fall into a region that is sensitive to the input, so as to avoid a gradient vanishing problem.

The pooling layer 904-2 may take an output of the convolutional layer 904-1 as an input. The pooling layer 904-2 may include a plurality of pooling nodes (e.g., E, F, G, and H), which may be used to sample the output of the convolutional layer 904-1, so as to reduce the computational load of data processing and accelerate the speed of data processing speed. In some embodiments, the size of the matrix representing the physiological data may be reduced in the pooling layer 904-2. The pooling layer 904-2 may improve the model classification and identification, provide nonlinearity, reduce the count of model parameters, and reduce the over-fitting problem.

The fully connected layer 904-N may include a plurality of neurons (e.g., 0, P, M, and N). The neurons may be connected to the pooling nodes in the pooling layer 904-2. In the fully connected layer 904-N, a plurality of vectors corresponding to the plurality of pooling nodes may be determined based on one or more features of the physiological data, and a plurality of weighting coefficients may be assigned to the plurality of vectors. Therefore, the fully connected layer 904-N may be configured to refit the tail of the CNN model to reduce the loss of feature information.

In some embodiments, a loss layer may be present (not shown) in the CNN model. The loss layer may include two inputs, one of which may be an estimated output of the CNN model and another may be a reference output (i.e., an actual output). The loss layer may perform a series of operations on these two inputs to obtain a cost function of the current network. The purpose of deep learning may be to find a weight that minimizes the cost function in a weight space. The cost function may be obtained in the forward propagation calculation, and also a beginning point of the back-propagation. The cost function may be basically composed of the estimated output and the reference output. The correct cost function may make the estimated output approximate to the reference output. In some embodiments, the cost function may include a Softmax cross entropy loss function or a square error loss function.

The output layer 906 may determine an output based on the vectors and the weighting coefficients obtained from the fully connected layer 904-N. In some embodiments, an output of the output layer 906 may include a probability map, a classification map, and/or a regression map. For example, the output of the output layer 906 may include a probability that a trigger condition is satisfied. As another example, the output of the output layer 906 may include a gating weighting function. More descriptions regarding the determination may be found in FIGS. 5, 7, and 8, and the descriptions thereof.

In some embodiments, adopting the CNN model for deep learning, the physiological data may balance the representation ability of the CNN model and the computational cost of training network. Furthermore, a batch normalization layer may be preferred in the embodiment. Compared with a local response normalization layer, the batch normalization layer may improve the gradient across CNN model and allow for a greater rate of learning, thereby increasing the speed of training.

In some embodiments, the CNN model may be implemented on one or more processing devices (e.g., the processing device 120). In some embodiments, a plurality of processing devices may execute a parallel processing operation in some layers of the CNN model 900 by, for example, assigning two or more processing devices for an operation of different nodes (e.g., a kernel, a pooling node, a neuron) in the CNN model 900. For example, a first GPU may execute the operation corresponding to the kernel A and kernel B, and a second kernel may execute the operation corresponding to the kernel C and kernel D. Similarly, a plurality of GPUs may also execute the operation of other nodes (e.g., a kernel, a pooling node, a neuron) in the CNN model 900. In addition, in some embodiments, a storage device (e.g., the storage device 130, the storage 220 of the computing device 200) may be provided for storing data related to the CNN model 900, such as activations and learned weights for each node.

It should be noted that the example in FIG. 9 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the CNN model 900 may include one or more additional components. Additionally or alternatively, one or more components of the CNN model 900 described above may be omitted. As another example, the CNN model 900 may include any number of layers and nodes.

FIG. 10 is a schematic diagram illustrating an exemplary ECG according to some embodiments of the present disclosure. The ECG may include a plurality of cycles indicating normal sinus rhythm. Generally, each cycle may include a P wave, a QRS complex, a T wave, as shown in FIG. 10. The QRS complex may include a Q wave, an R wave, and an S wave. As shown in FIG. 10, for each cycle of the ECG, a PR interval refers to a duration that extends from the beginning of the P wave to the beginning of the QRS complex. A PR segment refers to a duration that extends from the end of the P wave to the beginning of the QRS complex. A QT interval refers to a duration that extends from the beginning of the QRS complex to the end of the T wave. An ST segment refers to a duration that extends from the end of the QRS complex to the beginning of the T wave. As illustrated in FIG. 10, for the ECG, the R wave of the QRS complex may be the most significant wave among the components of one cycle of the ECG (e.g., the P wave, the QRS complex, the T wave). In some embodiments, the ECG may be analyzed by dividing one or more cardiac cycles. For example, an R wave may be designated as a beginning and/or an end of the cardiac cycle, which records the performance of the human heart from the beginning of one heartbeat to the end of the one heartbeat (or the beginning of a next heartbeat). A cardiac cycle may refer to a duration between two consecutive R waves. One cardiac cycle may be denoted as an R-R interval, or an R-R for short. A cardiac cycle may include a tension phase corresponding to a time period t1 from the peak of R wave to the end of T wave, and a resting (or relaxation) phase corresponding to a time period t2 from the end of T wave to the peak of R wave generated in the next cycle. The acquisition of image data (e.g., MR data) using a gating trigger technique as described in FIG. 8 may be performed during a time period (e.g., the middle to late stage) in the resting (or relaxation) phase (i.e., the time period t2). Accordingly, R waves may be to determine the tension phase and/or the resting (or relaxation) phase for imaging of movement subject (e.g., the heart). The trained machine learning model determined using a plurality of training samples may improve the accuracy and efficiency of R wave detection.

Figure 11:
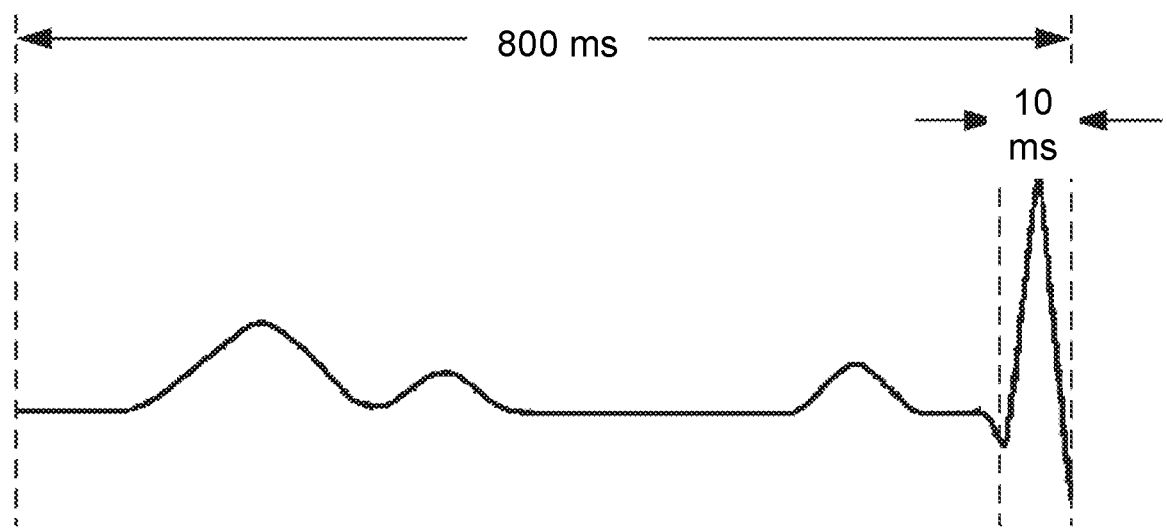
FIG. 11 is a schematic diagram illustrating first physiological data satisfying a trigger condition according to some embodiments of the present disclosure.
Figure 12:
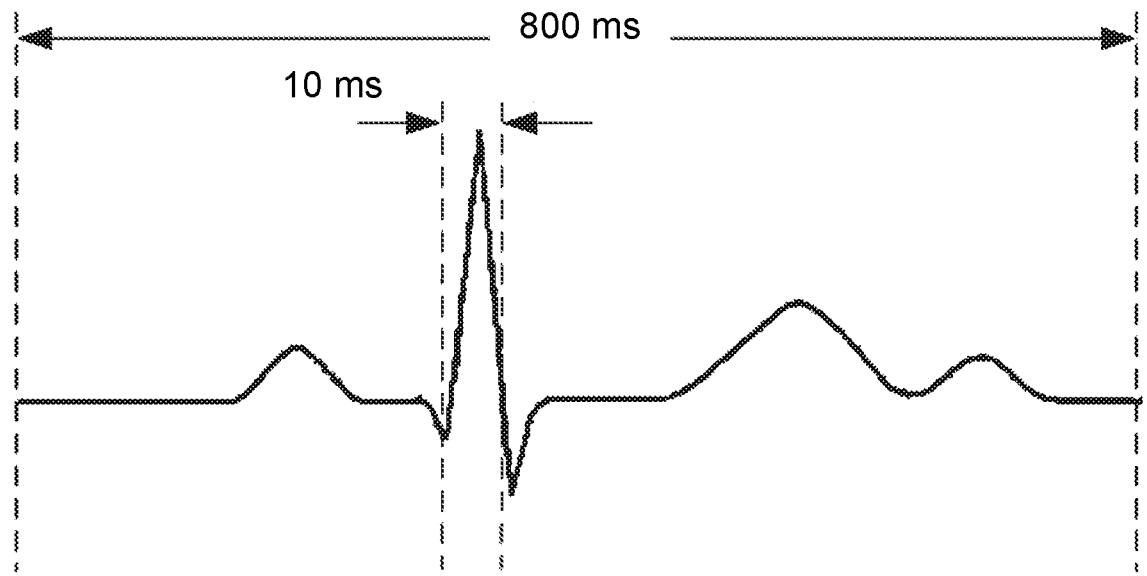
FIG. 12 is a schematic diagram illustrating second physiological data not satisfying a trigger condition according to some embodiments of the present disclosure.

FIG. 11 is a schematic diagram illustrating first physiological data satisfying a trigger condition according to some embodiments of the present disclosure. FIG. 12 is a schematic diagram illustrating second physiological data not satisfying the trigger condition according to some embodiments of the present disclosure.

As shown in FIG. 11 and FIG. 12, the lengths of the time periods of the first physiological data and the second physiological data are the same, 800 milliseconds, an average length of cardiac cycles. The first physiological data includes feature data (e.g., an R wave) located at a specific section (e.g., at the end of 10 milliseconds) of the time period of the first physiological data, i.e., the first physiological data satisfies a trigger condition. The second physiological data lacks feature data (e.g., the R wave) located at the specific section (e.g., at the end of 10 milliseconds) of the time period of the second physiological data, i.e., the second physiological data does not satisfy a trigger condition. The feature data may include position information associated with at least one of a peak of an R wave, a rising edge of the R wave, or a falling edge of the R wave in the ECG data. The specific section of the time period is at the end of 10 milliseconds of the time period of the first physiological data or the second physiological data.

In some embodiments, the first physiological data may be labeled as a positive training sample and the second physiological data fragment may be labeled as a negative training sample of the trained machine learning model as described elsewhere in the present disclosure (e.g., FIG. 6 and the descriptions thereof).

FIGS. 13A-13C are schematic diagrams illustrating an exemplary process for physiological data acquisition according to some embodiments of the present disclosure.

As shown in FIGS. 13A-13C, the physiological data may include ECG data. The ECG data are acquired by a monitoring device over time, and multiple extracted fragments (e.g., fragment 1, fragment 2, fragment 3) of ECG data may be acquired using a sliding window with width k and step length A. Each of the extracted fragments may be inputted into the trained machine learning model as described elsewhere in the present disclosure to obtain an output result. For example, the output result may include a positive value if the extracted fragment includes R wave located at the specific section (e.g., at the end of 10 milliseconds) of the time period of the extracted fragment.

FIG. 13A shows a current extracted fragment 1 obtained at a current time. FIG. 13B shows a next extracted fragment 2 adjacent to the current extracted fragment 1 acquired by the sliding window with step length λ1. As shown in FIG. 13B, the step length λ1 is less than the length of the time period m of the R wave in the ECG data. The extracted fragment 2 includes a portion of the R wave. FIG. 13C shows a next extracted fragment 3 immediately following the current extracted fragment 1 acquired by the sliding window with step length λ2. As shown in FIG. 13C, the step length λ2 is equal to the length of the time period m of the R wave in the ECG data. The extracted fragment 3 includes an integrated R wave.

The ECG data acquired before time point t or t+m has been acquired by the monitoring device, and the ECG data acquired after time point t or t+m has not been acquired by the monitoring device. In FIGS. 13A-13C only in order to describe the working process of the sliding window, the ECG data that has not been acquired are shown.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims.

Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device storing executable instructions, and
   at least one processor in communication with the at least one storage device, when executing the executable instructions, causing the system to perform operations including:
      acquiring physiological data of a subject, the physiological data corresponding to a motion of the subject over time;
      obtaining a trained machine learning model;
      determining, based on the physiological data, an output result of the trained machine learning model, the output result including a gating weighting function defined by a plurality of weighting values corresponding to the physiological data;
      obtaining original image data of the subject acquired by an imaging device synchronously with the acquisition of the physiological data by a monitoring device; and
      extracting image data from the original image data by multiplying the gating weighting function with the original image data.

2. The system of claim 1, wherein the physiological data includes at least one of electrocardiogram (ECG) data or respiration data.

3. The system of claim 1, wherein the output result further includes at least one of:
   the feature data represented in the physiological data; or
   a determination as to whether a trigger condition for triggering the imaging device to acquire the image data is satisfied.

4. The system of claim 3, wherein the feature data includes position information associated with at least one of a peak of an R wave, a rising edge of the R wave, a falling edge of the R wave in the physiological data, a peak of a P wave, a rising edge of the P wave, or a falling edge of the P wave in the physiological data.

5. The system of claim 3, wherein to obtain original image data of the subject acquired by an imaging device synchronously with the acquisition of the physiological data, the at least one processor is configured to cause the system to perform the operations including:
   in response to determining that the trigger condition is satisfied, generating, based on the output result, a trigger pulse signal; and
   causing, based at least in part on the trigger pulse signal, the imaging device to scan the subject to obtain the original image data of the subject.

6. The system of claim 5, wherein the trigger pulse signal includes a trigger delay for acquiring the original image data from a reference time point.

7. The system of claim 3, wherein to extract image data from the original image data, the at least one processor is configured to cause the system to perform the operations including:
   extracting, based on the feature data, the image data from the original image data.

8. The system of claim 1, wherein the physiological data is acquired by a monitoring device based on at least one of:
   an echo signal generated by emitting, by the monitoring device, an electromagnetic wave to the subject,
   an ECG signal,
   a photoelectric signal generated by emitting, by the monitoring device, light beams to the subject,
   an oscillation signal generated when the monitoring device detects an oscillation caused by a motion of the subject, or
   a pressure signal generated when the monitoring device detects a pressure change caused by the motion of the subject.

9. The system of claim 1, wherein the trained machine learning model is provided by a process including:
   obtaining a plurality of training samples;
   initializing parameter values of a machine learning model; and
   generating the trained machine learning model by iteratively updating, based on the plurality of training samples, the parameter values of the machine learning model.

10. The system of claim 9, wherein the iteratively updating, based on the plurality of training samples, the parameter values of the machine learning model includes:
    performing an iterative process, each iteration of the iterative process including:
       inputting at least one training sample of the plurality of training samples into the machine learning model;
       generating, based on the at least one training sample, an estimated output using the machine learning model;
       obtaining an assessment result by assessing a difference between the estimated output and a reference output corresponding to the at least one training sample;
       determining whether a termination condition is satisfied;
       based on a determination whether the termination condition is satisfied,
          updating, based on the assessment result, at least some of the parameter values of the machine learning model in response to the determination that the termination condition is not satisfied; or
          designating the machine learning model with the parameter values updated in a last iteration as the trained machine learning model in response to the determination that the termination condition is satisfied.

11. The system of claim 10, wherein the obtaining an assessment result by assessing a difference between the estimated output and a reference output includes:
determining a value of a cost function relating to the difference between the estimated output and the reference output.

12. The system of claim 11, wherein the cost function includes a Softmax cross entropy loss function or a square error loss function.

13. The system of claim 9, wherein the plurality of training samples include a plurality of positive samples and a plurality of negative samples, each of the plurality of positive samples includes first physiological data that includes feature data located within a specific section of a time period of the first physiological data, and each of the plurality of negative samples includes second physiological data that lacks the feature data located within the specific section of a time period of the second physiological data.

14. The system of claim 13, wherein a length of the specific section of the time period is less than a length of an acquisition window of the imaging device for acquiring the image data.

15. The system of claim 1, wherein to determine, based on the physiological data, an output result of a trained machine learning model, the at least one processor is configured to cause the system to perform the operations including:
performing a pretreatment operation on the physiological data to obtain preprocessed physiological data; and
generating the output result by inputting the preprocessed physiological data into the trained machine learning model.

16. The system of claim 15, wherein the pretreatment operation includes at least one of a normalization operation, a denoising operation, a smoothing operation, or a downsampling operation.

17. A system, comprising:
at least one storage device storing executable instructions, and
at least one processor in communication with the at least one storage device, when executing the executable instructions, causing the system to perform operations including:
obtaining a plurality of training samples, each of the plurality of training samples including physiological data of a subject; and
generating a trained machine learning model by training, based on the plurality of training samples, a machine learning model, wherein
the trained machine learning model is configured to perform:
determining, based on specific physiological data, a gating weighting function defined by a plurality of weighting values corresponding to the specific physiological data.

18. The system of claim 17, wherein to generate a trained machine learning model by training, based on the plurality of training samples, a machine learning model, the at least one processor is configured to cause the system to perform the operations including:
obtaining a plurality of training samples;
initializing parameter values of a machine learning model; and
generating the trained machine learning model by iteratively updating, based on the plurality of training samples, the parameter values of the machine learning model.

19. The system of claim 18, wherein the iteratively updating, based on the plurality of training samples, the parameter values of the machine learning model includes performing an iterative process, each iteration of the iterative process including:
inputting at least one training sample of the plurality of training samples into the machine learning model;
generating, based on the at least one training sample, an estimated output using the machine learning model;
obtaining an assessment result by assessing a difference between the estimated output and a reference output corresponding to the at least one training sample;
determining whether a termination condition is satisfied;
based on a determination whether the termination condition is satisfied,
updating, based on the assessment result, at least some of the parameter values of the machine learning model in response to the determination that the termination condition is not satisfied; or
designating the machine learning model with the parameter values updated in a last iteration as the machine learning model in response to the determination that the termination condition is satisfied.

20. A method, comprising:
acquiring physiological data of a subject, the physiological data corresponding to a motion of the subject over time;
obtaining a trained machine learning model;
determining, based on the physiological data, an output result of the trained machine learning model, the output result including a gating weighting function defined by a plurality of weighting values corresponding to the physiological data;
obtaining original image data of the subject acquired by an imaging device synchronously with the acquisition of the physiological data by a monitoring device; and
extracting image data from the original image data by multiplying the gating weighting function with the original image data.

* * * * *